(12) United States Patent
Inaba et al.

(10) Patent No.: US 7,153,412 B2
(45) Date of Patent: Dec. 26, 2006

(54) ELECTRODES, ELECTROCHEMICAL ELEMENTS, GAS SENSORS, AND GAS MEASUREMENT METHODS

(75) Inventors: Tadashi Inaba, Seto (JP); Keiichi Saji, Aichi-gun (JP); Tadashi Nakamura, Nagoya (JP); Yumi Masuoka, Aichi-gun (JP); Jiro Sakata, Nagoya (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 346 days.

(21) Appl. No.: 10/328,144

(22) Filed: Dec. 26, 2002

(65) Prior Publication Data
US 2003/0121801 A1 Jul. 3, 2003

(30) Foreign Application Priority Data
Dec. 28, 2001 (JP) ............................. 2001-400057
Jul. 8, 2002 (JP) ............................. 2002-198657

(51) Int. Cl.
*G01N 27/407* (2006.01)

(52) U.S. Cl. ................ 205/784.5; 205/781; 204/290.1; 204/291; 204/424; 204/425; 73/23.31

(58) Field of Classification Search ................ 204/424, 204/425, 290.1, 291; 205/781, 784.5, 787; 73/23.31, 23.32
See application file for complete search history.

(56) References Cited

U.S. PATENT DOCUMENTS

| | | | |
|---|---|---|---|
| 5,630,920 A | 5/1997 | Friese et al. | |
| 5,879,525 A | 3/1999 | Kato | |
| 6,051,123 A * | 4/2000 | Joshi et al. | .................. 204/424 |
| 6,060,420 A | 5/2000 | Munakata et al. | |
| 6,071,393 A * | 6/2000 | Oshima et al. | .............. 204/425 |
| 6,129,862 A | 10/2000 | Munakata et al. | |
| 6,379,514 B1 | 4/2002 | Schulte et al. | |
| 6,495,027 B1 * | 12/2002 | Stahl et al. | .................. 205/781 |
| 6,517,702 B1 * | 2/2003 | Stahl | ....................... 205/784.5 |
| 6,565,737 B1 * | 5/2003 | Marina et al. | ............... 205/765 |
| 6,586,127 B1 | 7/2003 | Ishihara et al. | |
| 6,844,098 B1 | 1/2005 | Ishihara et al. | |
| 6,942,772 B1 * | 9/2005 | Schneider et al. | .......... 204/424 |
| 7,052,595 B1 | 5/2006 | Schulte et al. | |
| 2002/0108870 A1 * | 8/2002 | Thoreson | ..................... 205/781 |

FOREIGN PATENT DOCUMENTS

| | | | |
|---|---|---|---|
| DE | 32 29 931 A1 * | 2/1983 | |
| DE | 198 39 382 A1 | 3/1999 | |
| DE | 199 32 048 A1 * | 1/2001 | |

(Continued)

OTHER PUBLICATIONS

Jakobs et al, Ionics 2 (1996), pp. 451-458.*

(Continued)

*Primary Examiner*—Kaj K. Olsen
(74) *Attorney, Agent, or Firm*—Oblon, Spivak, McClelland, Maier & Neustadt, P.C.

(57) ABSTRACT

Electrode having high activity to oxygen gas and low activity to flammable gas is provided. An oxygen pump includes oxide-ion conductive solid electrolyte 2, electrode 8 which is an inactive electrode, and active electrode 10. Electrode 8 is an electrode that includes $Ce_{0.8}Sm_{0.2}O_{2-\alpha}$. Electrode 8 is disposed on the gas detection chamber 12 side of solid electrolyte 2. Active electrode 10 is disposed on the open space side of solid electrolyte 2. Gas detection chamber 12 is an enclosed space defined by solid electrolyte 2, insulation layers 6, and diffusion control layer 4.

18 Claims, 24 Drawing Sheets

| | FOREIGN PATENT DOCUMENTS | | |
|---|---|---|---|
| DE | 199 27 725 C2 | 7/2001 | |
| DE | 199 60 338 A1 | 7/2001 | |
| EP | 0 188 868 A1 | 7/1988 | |
| JP | 6-14963 | 2/1994 | |
| JP | 6-267223 | 9/1994 | |
| JP | 08-130018 | 5/1996 | |
| JP | 10-325824 | 12/1998 | |
| JP | 11-271269 | 10/1999 | |
| JP | 2000-146905 | * | 5/2000 |
| JP | 2000-516223 | | 12/2000 |
| WO | WO 95/25277 | | 9/1995 |
| WO | WO 01/02845 | * | 1/2001 |

OTHER PUBLICATIONS

CAPLUS abstract for SU 1,247,740, Jul. 1986.*
Certified translation of JP 11-271,269, Oct. 1999.*
Inoue et al, J. Electrochem. Soc., 137 (8), pp. 2523-2527, 1990.*

* cited by examiner

ELECTRODES, ELECTROCHEMICAL ELEMENTS, GAS SENSORS, AND GAS MEASUREMENT METHODS

CROSS-REFERENCE

This application claims priority to Japanese patent application serial numbers 2001-400057, 2002-198657, the contents of which are hereby incorporated by reference as if fully set forth herein.

BACKGROUND OF THE INVENTION

1. Field of the Invention

The present invention relates to electrodes, electrochemical elements (e.g., oxygen pumps, electromotive force generation elements) and gas sensors. This invention also relates to gas measurement methods.

2. Description of the Related Art

It has been an important subject to reduce harmful gas components that are included in exhaust gas, which is emitted from various combustion apparatuses or combustion engines, as of automobile engines and boilers. In order to decrease the harmful gas components in exhaust gas, the combustion apparatuses or exhaust gas-purifying devices need to be controlled or monitored (e.g., catalyst deterioration has to be detected). In order to control or monitor the apparatuses, detecting devices that are capable of measuring concentrations of oxygen gas, flammable gas (e.g., various hydrocarbon gases), and nitrogen oxide gas ($NO_X$ gas) are required. Oxygen-pump for expelling oxygen gas from a gas detection chamber or introducing oxygen gas into the gas detection chamber is very useful for assembling the detecting devices. Known flammable gas sensors use an oxide-ion conductive solid electrolyte (e.g., yttria-stabilized zirconia (YSZ)) for forming at least a part of a wall surrounding a gas detection chamber. Voltage detecting type and current detecting type are known.

U.S. Pat. No. 5,879,525 teaches the current detecting type flammable gas sensor. As schematically shown in FIG. 25, the gas sensor includes oxide-ion conductive solid electrolyte 264, a pair of electrodes 252, 254, and a pair of electrodes 258, 260. Oxide-ion conductive solid electrolyte 264 (e.g., YSZ) forms a wall surrounding gas detection chamber 250. A pair of electrodes 252, 254 is provided at opposite faces of oxide-ion conductive solid electrolyte 264. Also, a pair of electrodes 258, 260 is provided at opposite faces of oxide-ion conductive solid electrolyte 264. A part of oxide-ion conductive solid electrolyte 264 and a pair of electrodes 252, 254 form first oxygen pump 256. A part of oxide-ion conductive solid electrolyte 264 and a pair of electrodes 258, 260 form second oxygen pump 262. First oxygen pump 256 adopts Pt electrode or Pt—Au electrode 254 (electrode that includes Pt or Pt—Au and a ceramic substance) within gas detection chamber 250.

At first, mixture gas of oxygen gas and flammable gas is introduced within gas detection chamber 250. Then electric voltage is applied between electrodes 252, 254 of first oxygen pump 256. While first oxygen pump 256 is being activated, oxygen gas existed within gas detection chamber 250 is expelled to the outside. Gas detection chamber 250 becomes almost free of oxygen gas after first oxygen pump 256 is activated. Next, second oxygen pump 262 is activated by applying voltage between electrodes 258, 260 of second oxygen pump 262. While second oxygen pump 262 is being activated, oxygen gas is introduced to gas detection chamber 250 and flammable gas is oxidized with the introduced oxygen gas. A quantity of oxygen gas introduced for oxidizing flammable gas within gas detection chamber 250 is proportional to value of current flowing through second oxygen pump 262.

In this gas sensor, the Pt electrode or Pt—Au electrode 254 is disposed within gas detection chamber 250. However, the Pt electrode and Pt—Au electrode have activity not only to oxygen gas but also to flammable gas (various hydrocarbons, etc). This causes oxidization of flammable gas while first oxygen pump 256 is activated. That is, a portion of flammable gas is oxidized while first oxygen pump 256 is activated for expelling oxygen gas from gas detection chamber 250. Consequently, the second oxygen pump 262 introduces less quantity of oxygen gas than a quantity of oxygen required to oxidize flammable gas that were included within gas detection chamber 250 before first oxygen pump 256 was activated. As a result, second oxygen pump 262 cannot measure flammable gas concentration accurately.

Also, known nitrogen oxide gas sensors include first oxygen pump and second oxygen pump, both of which have oxide-ion conductive solid electrolyte. Some of the gas sensors use a Pt—Au electrode for forming first oxygen pump, and the Pt—Au electrode is disposed within gas detection chamber.

At first, mixture gas of oxygen gas and nitrogen oxide gas is introduced within gas detection chamber. Then electric voltage is applied between electrodes of first oxygen pump. While first oxygen pump is being activated, oxygen gas existed within gas detection chamber is expelled to the outside. Gas detection chamber becomes almost free of oxygen gas after first oxygen pump is activated. Next, second oxygen pump is activated by applying voltage between electrodes of second oxygen pump. While second oxygen pump is being activated, nitrogen oxide gas within gas detection chamber is decomposed (i.e., reductive reaction) into nitrogen gas and oxygen gas. Decomposed oxygen gas is expelled to the outside. When oxygen is conducted through oxide-ion conductive solid electrolyte of second oxygen pump, current flows between electrodes of second oxygen pump. A quantity of oxygen gas expelled by second oxygen pump is proportional to value of current flowing through second oxygen pump. Based on a quantity of oxygen gas decomposed from nitrogen oxide gas, nitrogen oxide gas concentration can be calculated.

In this gas sensor, the Pt—Au electrode of first oxygen pump disposed within gas detection chamber has activity only with oxygen gas and does not affect to nitrogen oxide gas within gas detection chamber, as long as the voltage applied to first oxygen pump is low. Accordingly, when the voltage applied to first oxygen pump is low, only oxygen can be pumped out and pumping by first oxygen pump provides with little influence upon the nitrogen oxide gas. However, when the voltage applied to first oxygen pump increases, the activity of the Pt—Au electrode to nitrogen oxide gas increases. As a result, accuracy of nitrogen oxide gas concentration measurement by second oxygen pump degrades.

In a case that both of flammable gas concentration and nitrogen oxide gas concentration within mixture gas of oxygen gas, flammable gas, and nitrogen oxide gas are required to be measured, oxygen gas within gas detection chamber must be expelled from gas detection chamber by activating oxygen pump. The electrode of the oxygen pump is required to have low activity to both flammable gas and nitrogen oxide gas. However, the aforesaid Pt electrode has activity to both flammable gas and nitrogen oxide gas. In the aforesaid Pt—Au electrode, the activity to the nitrogen oxide gas is low, however, the activity to flammable gas is high. As mentioned above, electrodes that have high activity to oxygen gas and low activity to flammable gas and nitrogen oxide gas have not been found yet. Thus, when a gas subject to gas concentration measurement contains flammable gas and nitrogen oxide gas, the known techniques cannot measure the concentrations of these gases with high accuracy.

SUMMARY OF THE INVENTION

It is, accordingly, an object of the present teachings to provide electrodes that have high activity to oxygen gas and low activity to flammable gas and/or nitrogen oxide gas.

Another object of the present teachings is to provide electrochemical elements (oxygen pumps) that can expel or introduce oxygen gas within mixture gas having oxygen gas and flammable gas and/or nitrogen oxide gas, while minimizing influence upon flammable gas and/or nitrogen oxide gas.

A further object of the present teachings is to provide techniques that can highly accurately measure a quantity (concentration) of flammable gas and/or nitrogen oxide gas within mixture gas having oxygen gas and flammable gas and/or nitrogen oxide gas. The present teachings provide new electrochemical elements, gas sensors, and gas measurement methods.

In one aspect of the present teachings, an electrode may include at least one component selected from a group consisting of (I) to (IV);
(I) a perovskite oxide expressed by $(A_{1-x}B_x)(C_{1-y}D_y)O_{3-z}$,
(II) an oxide expressed by $(Ce_{1-x}P_x)O_{2-z}$,
(III) a mixture of said (I) and said (II), the proportion of said (II) in the mixture being 1 to 95% by weight, and
(IV) a layered body formed by at least two layers, each layer including at least one component selected from a group consisting of said (I), said (II) and the mixture of said (I) and (II).

In (I) through (IV), symbol indicates as follows;
symbol A represents La, Pr, Ce, Ca, Sr, or Ba;
symbol B represents Sr, Ce or Ca;
symbol C represents Cr, Mn, Fe, Co, Ti, Zr, or Ga;
symbol D represents Cr, Ni, Mg, Zr, Ce, Fe, Al, or Co, and
symbol P represents La, Pr, Nd, Sm, Eu, Gd, Tb, Dy, Tm, Yb, Ca, Y, Mg, Sr, Ba, Zr, Mn, Fe, or Cr. Symbol X satisfies the condition of $0 \leq X \leq 0.5$. Symbol Y satisfies the condition of $0 \leq Y \leq 0.5$.

As a result of the present inventors' intensive studies to attain the above objects it has been found that the aforesaid electrode (hereinafter called "oxide-containing electrode") has high activity to oxygen gas and low activity to flammable gas and nitrogen oxide gas. That is, activity of oxide-containing electrode for promoting reaction between oxygen gas and flammable gas is low. Also, activity of oxide-containing electrode for promoting decomposition of nitrogen oxide gas into nitrogen gas and oxygen gas is low.

In another aspect of the present teachings, an electrochemical element (e.g., an oxygen pump, an electromotive force generation element) may include an oxide-ion conductive solid electrolyte, and the aforesaid oxide-containing electrode. The oxide-ion conductive solid electrolyte and the oxide-containing electrode may be in contact with each other or may be next to each other with another member between them.

The electrochemical element (the oxygen pump) has the aforesaid oxide-containing electrode. Accordingly, even if not only oxygen but also flammable gas and/or nitrogen oxide gas are included in the ambient atmosphere, the oxygen pump is capable of selectively expelling or introducing the oxygen while minimizing influence upon flammable gas and/or nitrogen oxide gas.

The electrochemical element (the electromotive force generation element) generates voltage between the electrodes when the oxide-containing electrode and the other electrode are exposed to gas that includes flammable gas. The voltage may be changed in accordance with flammable gas concentration. Because the element includes the aforesaid oxide-containing electrode, even if the measuring atmosphere contains flammable gas as well as oxygen, a oxidation reaction of flammable gas hardly occurs at the oxide-containing electrode. Accordingly, this electromotive force generation element enables a quantity (concentration) of flammable gas to be measured with high accuracy by the voltage generated between the oxide containing electrode and the other electrode.

In another aspect of the present teachings, a gas sensor may include an oxide-ion conductive solid electrolyte and a first electrode and a second electrode. The oxide-ion conductive solid electrolyte may form at least a part of a wall surrounding a gas detection chamber. The first electrode may be the aforesaid oxide-containing electrode. The first electrode may be disposed within the gas detection chamber. The oxide-ion conductive solid electrolyte and the first electrode may be in contact with each other or are next to each other with another member between them. The second electrode may be disposed within the gas detection chamber. The oxide-ion conductive solid electrolyte and the second electrode may be in contact with each other or are next to each other with another member between them. The second electrode may be active to promote oxidation of flammable gas or reduction of nitrogen oxide gas. The gas detection chamber may include a plurality of chamber parts as a matter of course.

In another aspect of the present teachings, a gas measurement method is taught. The method may include introducing mixture gas into the gas detection chamber under a predetermined diffusion resistance and measuring a difference or a ratio between a limiting current flowing a first oxygen pump and a limiting current flowing a second oxygen pump. The first oxygen pump may include the aforesaid oxide-containing electrode in the gas detection chamber. The second oxygen pump may include a electrode being active to promote oxidation of flammable gas or reduction of nitrogen oxide gas in the gas detection chamber.

According to these aspects, when oxygen and flammable gas or nitrogen oxide gas are present, a quantity (concentration) of the flammable gas or the nitrogen oxide gas can be highly accurately measured by a difference in limiting current between the first oxygen pump and the second oxygen pump.

Another representative gas sensor may include an oxide-ion conductive solid electrolyte, the aforesaid oxide-containing electrode, and a first measurement element. The oxide-ion conductive solid electrolyte may form at least a part of a wall surrounding a gas detection chamber. The oxide-containing electrode may be disposed within the gas detection chamber. The oxide-ion conductive solid electrolyte and the oxide-containing electrode may be in contact with each other or are next to each other with another member between them. The first measurement element may measure a quantity (typically by the form of concentration) of flammable gas or nitrogen oxide gas in the gas detection chamber.

Another representative gas measurement method may include: introducing mixture gas into a gas detection chamber under a predetermined diffusion resistance; and expelling or introducing oxygen in the gas detection chamber by utilizing a first oxygen pump. The first oxygen pump may include the aforesaid oxide-containing electrode disposed within the gas detection chamber. The method may include measuring a quantity (typically by the form of concentration) of flammable gas or nitrogen oxide gas in the gas detection chamber.

In these aspects, the gas sensor or the first oxygen pump has the aforesaid oxide-containing electrode. Accordingly, when mixture gas of oxygen and flammable gas or nitrogen oxide gas are present, the gas sensor or the first oxygen pump is capable of selectively decreasing or increasing the oxygen in the mixture gas, with little influence upon the flammable gas or the nitrogen oxide gas. Accordingly, the quantity (concentration) of the flammable gas or the nitrogen oxide gas can be measured with high accuracy.

DETAILED DESCRIPTION OF THE PREFERRED EMBODIMENT

First Detailed Representative Embodiment

Figure 1:
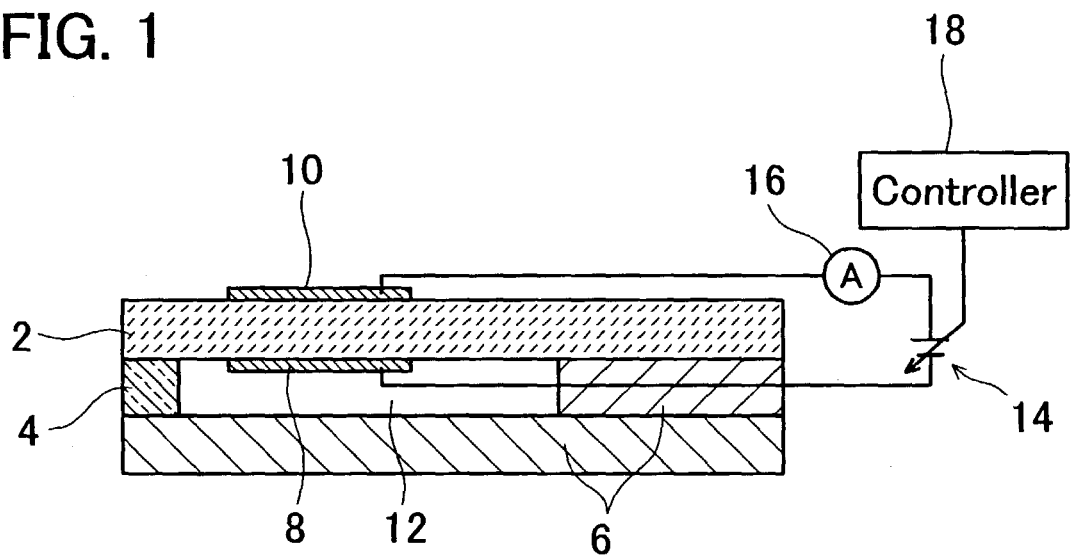
FIG. 1 is a schematic cross-sectional view of an electrochemical oxygen pump according to the second representative embodiment of the present teachings.

An electrode according to the first embodiment of the present invention is an electrode that includes at least one component selected from a group consisting of (I) to (IV) (hereinafter referred to as "oxide-containing electrode"). This oxide-containing electrode may contain another constituent if necessary.

(I) A perovskite oxide expressed by $(A_{1-x}B_x)(C_{1-y}D_y)O_{3-z}$ (II) An oxide expressed by $(Ce_{1-x}P_x)O_{2-z}$ (III) A mixture of said (I) and said (II), the proportion of said (II) in the mixture being 1 to 95% by weight (IV) A layered body formed by at least two layers, each layer including at least one component selected from a group consisting of said (I), said (II) and the mixture of said (I) and (II)

In (I) through (IV), symbol A represents lanthanum (La), praseodymium (Pr), cerium (Ce), calcium (Ca), strontium (Sr), or barium (Ba). Symbol B represents strontium (Sr), cerium (Ce), or calcium (Ca). Symbol C represents chromium (Cr), manganese (Mn), iron (Fe), cobalt (Co), titanium (Ti), zirconium (Zr), or gallium (Ga). Symbol D represents chromium (Cr), nickel (Ni), magnesium (Mg), zirconium (Zr), cerium (Ce), iron (Fe), aluminum (Al), or cobalt (Co). Symbol P represents lanthanum (La), praseodymium (Pr), neodymium (Nd), samarium (Sm), europium (Eu), gadolinium (Gd), terbium (Tb), dysprosium (Dy), thulium (Tm), ytterbium (Yb), calcium (Ca), yttrium (Y), magnesium (Mg), strontium (Sr), barium (Ba), zirconium (Zr), manganese (Mn), iron (Fe), or chromium (Cr).

The aforesaid oxide-containing electrode is preferably a porous electrode having porosity that allows the diffusion of gas molecules, in order to increase the specific surface area of the electrode, supply gas molecules into the electrode layer, and effectively use reaction active sites that exist in the electrode layer. Therefore, it is preferable that the electrode be made of particles having a particle diameter of 0.05 to 200 μm and the porosity of the electrode be 10 to 60%. In view of film strength, it is more preferable that the particle diameter be 0.2 to 100 μm and the porosity of the electrode be 20 to 50%.

In the oxide shown in (I), symbol A or B preferably represents La, Pr, Ca, or Sr. Also, symbol C or D preferably represents Cr, Mn, Fe, Co, Ga, or Ni. In the oxide shown in (II), symbol P preferably represents Pr, Sm, Gd, Tb, Ca, Zr, or Mn. Similarly, these elements are preferably utilized in the mixture shown in (III) and the layered body shown in (IV).

Additionally, in each of (I) and (IV), symbols X and Y represent the following ranges. X satisfies the condition of $0 \leq X \leq 0.5$, preferably $0.1 \leq X \leq 0.4$. Y satisfies the condition of $0 \leq Y \leq 0.5$, preferably $0 \leq Y \leq 0.3$. Symbols Z preferably satisfies $-0.5 \leq Z \leq 0.5$ more preferably $-0.1 \leq Z \leq 0.1$. Symbol Z in each oxide formula represents a number and, in this specification, the number is α. The aforesaid oxide-containing electrode may include only the oxide shown in (I) and/or the oxide shown in (II). However, besides these oxides, the oxide-containing electrode may also include another constituent, such as Pt, Pd, Au, or YSZ.

Preferred examples of the oxides that are shown in (I) and (II) are listed in Table 1 below.

TABLE 1

| | Electrode Material |
|---|---|
| Simple Body | $Ce_{0.8}Sm_{0.2}O_{2-\alpha}$ |
| | $Ce_{0.8}Pr_{0.2}O_{2-\alpha}$ |
| | $Ce_{0.9}Ca_{0.1}O_{2-\alpha}$ |
| | $Ce_{0.8}Gd_{0.2}O_{2-\alpha}$ |
| | $Pr_{0.6}Sr_{0.4}MnO_{3-\alpha}$ |
| | $La_{0.6}Sr_{0.4}MnO_{3-\alpha}$ |
| | $La_{0.8}Sr_{0.2}CrO_{3-\alpha}$ |
| | $La_{0.6}Sr_{0.4}Co_{0.95}Ni_{0.05}O_{3-\alpha}$ |
| | $Pr_{0.6}Sr_{0.4}Mn_{0.95}Ni_{0.05}O_{3-\alpha}$ |
| | $SrTi_{0.6}Fe_{0.4}O_{3-\alpha}$ |
| | $La_{0.8}Ca_{0.2}CoO_{3-\alpha}$ |
| | 90% by mass of $SrTi_{0.6}Fe_{0.4}O_{3-\alpha}$ + 9.8% by mass of Pt + 0.2% by mass of Au |

The mixture shown in (III) includes the oxide shown in (I) and the oxide shown in (II), and the proportion of (II) to (I)+(II) is 1 to 95% by weight. Particularly, the proportion of (II) to (I)+(II) is preferably 30 to 80% by mass in terms of, e.g., adhesion to the oxide-ion conductive solid electrolyte. The mixture that is shown in (III) may also include another constituent, such as Platinum (Pt), Palladium (Pd), Gold (Au), or stabilized zirconia, if required.

Table 2 below gives preferred examples of the mixture that is shown in (III).

TABLE 2

| | Electrode Material |
|---|---|
| Mixture | 25% by mass of $Pr_{0.6}Sr_{0.4}MnO_{3-\alpha}$ + 75% by mass of $Ce_{0.8}Sm_{0.2}O_{2-\alpha}$ |
| | 50% by mass of $Pr_{0.6}Sr_{0.4}MnO_{3-\alpha}$ + 50% by mass of $Ce_{0.8}Sm_{0.2}O_{2-\alpha}$ |
| | 75% by mass of $Pr_{0.6}Sr_{0.4}MnO_{3-\alpha}$ + 25% by mass of $Ce_{0.8}Sm_{0.2}O_{2-\alpha}$ |
| | 50% by mass of $Pr_{0.6}Sr_{0.4}Mn_{0.95}Ni_{0.05}O_{3-\alpha}$ + 50% by mass of $Ce_{0.8}Sm_{0.2}O_{2-\alpha}$ |
| | 50% by mass of $La_{0.8}Sr_{0.2}CrO_{3-\alpha}$ + 50% by mass of $Ce_{0.8}Sm_{0.2}O_{2-\alpha}$ |
| | 50% by mass of $La_{0.8}Sr_{0.2}MnO_{3-\alpha}$ + 50% by mass of $Ce_{0.8}Pr_{0.2}O_{2-\alpha}$ |
| | 50% by mass of $La_{0.6}Sr_{0.4}Co_{0.95}Ni_{0.05}O_{3-\alpha}$ + 50% by mass of $Ce_{0.8}Sm_{0.2}O_{2-\alpha}$ |
| | 45% by mass of $La_{0.6}Sr_{0.4}CrO_{3-\alpha}$ + 45% by mass of $Ce_{0.8}Sm_{0.2}O_{2-\alpha}$ + 9.8% by mass of Pt + 0.2% by mass of Au |
| | 45% by mass of $La_{0.8}Sr_{0.2}CrO_{3-\alpha}$ + 45% by mass of $Ce_{0.8}Sm_{0.2}O_{2-\alpha}$ + 10% by mass of YSZ |

The layered body that is shown in (IV) is formed by at least two layers, each layer including at least one component selected from the group consisting of a layer of the oxide shown in (I), a layer of the oxide shown in (II), and the mixture of the oxides shown in (I) and (II). The preferred examples of such a layered body are as follows: the layered body of [a layer of a mixture of 25% by mass of $Pr_{0.6}Sr_{0.4}MnO_{3-\alpha}$ and 75% by mass of $Ce_{0.8}Sm_{0.2}O_{2-\alpha}$] and [a layer of a mixture of 50% by mass of $Pr_{0.6}Sr_{0.4}MnO_{3-\alpha}$ and 50% by mass of $Ce_{0.8}Sm_{0.2}O_{2-\alpha}$]; the layered body of [a layer of $Ce_{0.8}Sm_{0.2}O_{2-\alpha}$] and [a layer of a mixture of 50% by mass of $Ce_{0.8}Sm_{0.2}O_{2-\alpha}$ and 50% by mass of $Pr_{0.6}Sr_{0.4}MnO_{3-\alpha}$]; layered body of [a layer of $Ce_{0.9}Ca_{0.1}O_{2-\alpha}$] and [a layer of $Pr_{0.6}Sr_{0.4}MnO_{3-\alpha}$]; and a layered body of [a layer of $Ce_{0.8}Sm_{0.2}O_{2-\alpha}$] and [a layer of $La_{0.6}Sr_{0.4}Co_{0.95}Ni_{0.05}O_{3-\alpha}$].

Among (I) to (IV), the mixtures shown in (III) and the layered body shown in (IV) are preferable in order to decrease electrode reaction resistance that accompanies a gas reaction. The mixture shown in (III), which is capable of decreasing the electrode reaction resistance greater than the layered body, is particularly preferable.

In order to improve responsiveness, the above described oxide-containing electrode may contain at least Pt, Pd, Rh, Ag, Ni, or Au, in the case of which a content of 0.1 to 50% by mass is preferable to the total mass of the oxide shown in (I), to the total mass of the oxide shown in (II), or to the total mass of the mixture thereof. A content of 0.1 to 20% by mass is more preferable.

The aforesaid oxide-containing electrode can be fabricated such that the oxide shown in (I), which was described above, the oxide shown in (II), which was described above, or the mixture of the oxides (I) and (II) is kneaded into a paste by means of e.g., a roll mill after a binder or the like is added, if necessary, and then the prepared paste was screen printed onto a green sheet. In the alternative, the oxide-containing electrode can be formed on an oxide-ion conductive solid electrolyte substrate by an evaporation method, sputtering method, sol-gel method, or the like. The size and shape of the electrode may be suitably selected in accordance with the size and shape of, e.g., a gas sensor, which will be described later. Examples of the binder are polyvinyl alcohol, triton X, cellulose. If required, alcohol, ether, water, etc. may be added.

The oxide-containing electrode according to the representative embodiment that was described above has high activity to an oxygen gas and has low activity to flammable gas and nitrogen oxide gas. By virtue of the properties, in the oxide-containing electrode, the combustion reactivity of the oxygen and the flammable gas is low and the reduction reactivity of the nitrogen oxide gas is also low. Further, in the electrode, the reactivity of the flammable gas and the nitrogen oxide gas is low.

Additionally, each oxygen pump, in which the oxide-containing electrode of the present embodiment is formed on the oxide-ion conductive solid electrolyte, remarkably decreases electrode reaction resistance that accompanies oxygen ionization, which occurs on an interface between the solid electrolyte and the electrode. Some oxygen pumps are capable of decreasing the resistances of the elements by one or more digits in comparison to the known oxygen pumps. Accordingly, even if a low voltage is applied to the oxygen pump, a large quantity of oxygen can be pumped. In addition, quick response can be yielded. Thus, by utilizing the oxide-containing electrode of the present embodiment, the oxygen pump that has a high ability to pump oxygen or a high ability to control the oxygen concentration can be formed.

U.S. Pat. No. 5,879,525 (PCT No. PCT/DE95/00253) and PCT No. PCT/DE95/00255 disclose another gas sensors. In the gas sensors, a pair of electrodes, one of which contains platinum (Pt) and bismuth (Bi), is formed on an oxide-ion conductive solid electrolyte and a potential difference between the electrodes, which occurs by a catalytic activity difference between the electrodes, is measured as an electromotive force. These sensors are designed to enhance the ability to select and detect hydrocarbon, by including Bi in Pt in order to decrease the catalytic activity of Pt considerably. However, because the fusing point of Bi is low, baking the layered body into one piece is difficult and long use at high temperatures is also difficult.

Contrarily, the oxide-containing electrode of the present embodiment is chemically stable even in the ambient atmosphere (e.g., exhaust gas) that contains oxygen, flammable gas and/or nitrogen oxide gas. Also, this electrode can be used at high temperatures for a long period of time and is highly durable.

Second Detailed Representative Embodiment

As shown in FIG. 1, an electrochemical oxygen pump includes: oxide-ion conductive solid electrolyte 2; oxide-containing electrode 8 of the first embodiment, which is an inactive electrode; and active electrode 10. The oxygen pump may be referred to as a oxygen pump element or a oxygen pump cell, or may be referred to as an electrochemical element in the highest concept. Oxide-containing electrode 8 is disposed, provided, or formed on the gas detection chamber 12 side of solid electrolyte 2. Active electrode 10 is disposed on the open space side of solid electrolyte 2. Gas detection chamber 12 is an enclosed space defined by solid electrolyte 2, insulation layers 6, and diffusion control layer 4.

Oxide-containing electrode 8 and active electrode 10 are electrically coupled via ammeter 16 and voltage source 14. An anode of voltage source 14 is coupled to active electrode 10, and a cathode thereof is coupled to oxide-containing electrode 8. To voltage source 14, a controller (e.g., computer or control circuit) 18 is connected in order to control a voltage of voltage source 14.

Solid electrolyte 2 and oxide-containing electrode 8 may be directly bonded together by an adhesive or the like. solid electrolyte 2 and oxide-containing electrode 8 may be near to each other with another member (e.g., metallic material or solid electrolyte) disposed between electrolyte 2 and electrode 8. In the alternative, oxide-containing electrode 8 may not be bonded, joined, or fixed to solid electrolyte by an adhesive. For example, oxide-containing electrode 8 may be simply placed on solid electrolyte 2.

Any solid electrolyte that is oxide-ion conductive can be utilized as solid electrolyte 2. Examples of such solid electrolyte are: a zirconium solid electrolyte ($ZrO_2$-$M_2O_3$ solid solution or $ZrO_2$-MO solid solution, wherein symbol M represents yttrium (Y), ytterbium (Yb), gadolinium (Gd), calcium (Ca), magnesium (Mg), etc); and a ceria solid electrolyte ($CeO_2$-$M_2O_3$ solid solution or $CeO_2$-M solid solution, wherein symbol M represents yttrium (Y), samarium (Sm), etc). Of these solid electrolytes, the zirconium solid electrolyte is preferable in terms of stability and oxide-ion conductivity in an exhaust gas. In particular, $ZrO_2$ in which 3 to 8 mol % $Y_2O_3$ is present in the form of a solid solution is preferable.

Each insulation layer 6 preferably includes a material that has high insulation resistance at the oxygen pumping temperature of the solid electrolyte. Preferable examples of such a material are alumina, spinel, mullite, and cordierite.

Next, a method for controlling oxygen partial pressure (concentration) by utilizing the oxygen pump will be explained with reference to FIG. 1. The ambient atmosphere (gas) containing flammable gas (e.g., hydrocarbon) and/or nitrogen oxide gas, which is present in open space, is introduced into gas detection chamber 12 via diffusion control porous layer 4 under a predetermined diffusion resistance. Then, a voltage is applied by voltage source 14. As a result, the oxygen in the gas detection chamber 12 is ionized by the oxygen pumping action of the oxygen pump. The oxygen ions are expelled (discharged) from the gas detection chamber 12, via oxide-containing electrode 8, solid electrolyte 2, and active electrode 10, into the open space. A pumping current flows in, e.g., solid electrolyte 2 in accordance with a quantity of expelled oxygen.

Accordingly, by measuring the current by ammeter 16, the quantity of expelled oxygen can be found. The quantity of oxygen that is expelled may be varied in accordance with a voltage of voltage source 14. Controlling the voltage of voltage source 14 by controller 18 can control the oxygen partial pressure (oxygen concentration) in the gas detection chamber 12. Thus, the oxygen pump according to the present embodiment can be utilized as, for example, an oxygen concentration control element.

The oxygen pump includes oxide-containing element 8, which was described in detail above. Even if the ambient atmosphere contains not only oxygen but also flammable gas and/or nitrogen oxide gas, a large quantity of oxygen can be selectively expelled (discharged) or introduced by the application of a low voltage while the influence on the flammable gas and/or nitrogen oxide gas is minimized. Moreover, fast response is yielded. Accordingly, the oxygen pump has a high ability to pump oxygen or to control oxygen concentration. Further, because the oxygen pump includes the foregoing oxide-containing electrode 8, chemical stability and high durability are assured. Therefore, the oxygen pump can be stably utilized for a long period of time even in an ambient atmosphere containing not only oxygen but also flammable gas and/or nitrogen oxide gas.

Accordingly, the oxygen pump is useful as an oxygen concentration control element, which selectively controls the oxygen concentration in, e.g., a gas flow passage or an enclosed space. In particular, the oxygen pump can be utilized in a gas sensor that is capable of improving its measurement accuracy by controlling the oxygen concentration. Examples of the gas sensor are a known flammable gas sensor, nitrogen oxide ($NO_X$) gas sensor, and resistance type gas sensor that uses an oxide semiconductor.

Third Detailed Representative Embodiment

Figure 2:
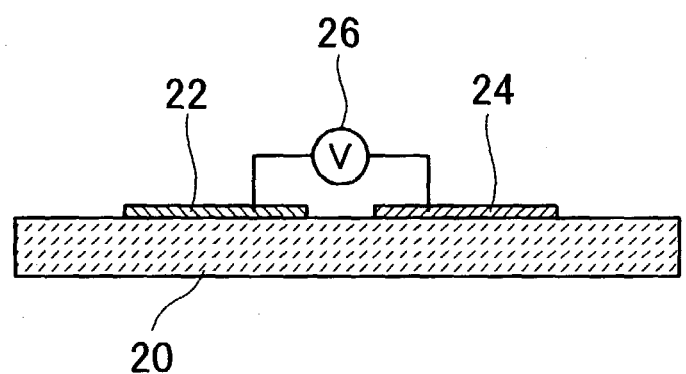
FIG. 2 is a schematic cross-sectional view of an electromotive force generation element according to the third representative embodiment of the present teachings.

As shown in FIG. 2, an electromotive force generation element according to the third embodiment of the present invention includes solid electrolyte 20 that is oxide-ion conductive, oxide-containing electrode 22 that is an inactive electrode, and active electrode 24. The electromotive force generation element may be referred to as an electrochemical element in the highest concept. Oxide-containing electrode 22 and active electrode 24 are disposed on one side of solid electrolyte 20 and are electrically coupled via voltmeter 26.

When the electromotive force generation element is placed in an ambient atmosphere that contains oxygen and flammable gas (e.g., hydrocarbon gas) as well, the oxygen concentration near active electrode 24 decreases due to catalysis. On the other hand, the oxygen concentration near oxide-containing electrode 22 (the inactive electrode) hardly changes. Consequently, a difference in oxygen concentration occurs between active electrode 24 and oxide-containing electrode 22. As a result, due to the difference in electrode activity between electrodes 22, 24, electromotive force generation element generates an electromotive force according to the oxygen concentration difference. The electromotive force changes with the flammable gas concentration. Thus, the electromotive force generation element enables the flammable gas concentration to be measured by the electromotive force generated between electrodes 22, 24. In particular, if a difference in activity between electrodes 22, 24 is large relative to only a hydrocarbon gas, the electromotive generation element functions as a hydrocarbon gas sensor.

The electromotive force generation element includes oxide-containing electrode 22, which was discussed above. Even if the ambient atmosphere contains both oxygen and the flammable gas, the concentration of the flammable gas can be measured highly accurately and rapidly (yielding a fast response) by the value of the generated electromotive force. Moreover, including foregoing oxide-containing electrode 22, the electromotive force generation element is chemically stable and highly durable.

The oxygen pump and electromotive force generation element according to the representative embodiments of the present invention may be used individually or in combination. In the alternative, the oxygen pump and the electromotive force generation element may be used in combination with another known element (e.g., gas concentration measurement element). If a single solid electrolyte can be shared between two or more elements, pairs of electrodes may be formed on the single solid electrolyte in order to obtain, e.g., a composite-type of gas sensor.

Fourth Detailed Representative Embodiment

Figure 3:
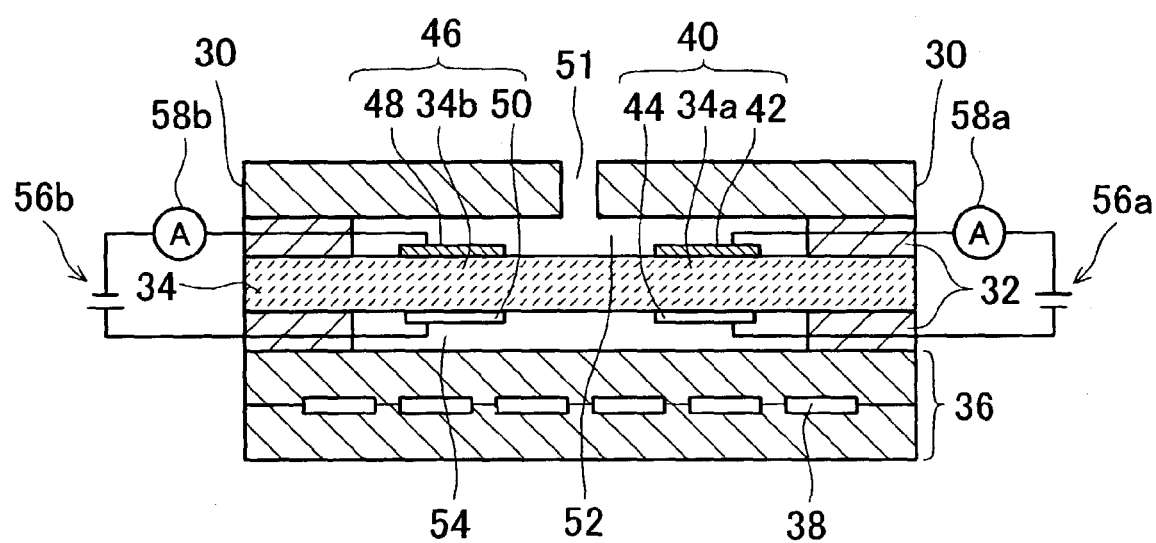
FIG. 3 is a schematic cross-sectional view of a gas sensor according to the fourth representative embodiment of the present teachings.

As shown in FIG. 3, a gas sensor according to the fourth embodiment of the present invention includes first oxygen pump 40, second oxygen pump 46, insulation layers 30, 32, 36, heater 38, voltage source 56a, 56b, and ammeter 58a, 58b. The gas sensor may be referred to as a gas concentration measurement device, a gas constituent measurement device, a gas concentration detection sensor, etc. This assertion applies to the other embodiments of the present invention.

First oxygen pump 40 has: first solid electrolyte 34a, which is an oxide ion conductor; oxide-containing electrode 42, which was described in the above-illustrated embodiments; and Pt electrode 44. Oxide-containing electrode 42 is disposed on gas detection chamber 52 side of first solid electrolyte 34a. Pt electrode 44 is disposed on the reference-gas introducing chamber 54 side of first solid electrolyte 34a. Gas detection chamber (space) 52 may be referred to as "gas introducing chamber (space)" or "gas accommodating chamber (space)". This assertion applies to the other embodiments of the present invention.

Second oxygen pump 46 has: second solid electrolyte 34b, which is an oxide ion conductor; active electrode 48, which is active to a catalytic reaction of flammable gas and oxygen or which is active to an electrochemical reductive reaction of nitrogen oxide gas; and Pt electrode 50. Active electrode 48 is disposed on gas detection chamber 52 side of second solid electrolyte 34b. Pt electrode 50 is disposed on the reference-gas introducing chamber 54 side of second solid electrolyte 34b. Active electrode 48 preferably contains at least platinum (Pt), palladium (Pd), rhodium (Rh), silver (Ag), nickel (Ni), or gold (Au), from the viewpoint on the flammable gas (in particular, a hydrocarbon gas) or nitrogen oxide gas selectivity. It is more preferable for active electrode 48 to contain the above selected element as its main constituent.

Gas detection chamber 52 is an enclosed space defined by solid electrolyte 34 and insulating layers 30, 32. Gas diffusion hole 51 is defined in insulation layer 30. Insulation layer 30 functions as a diffusion control body. The gas sensor preferably includes the diffusion control body, as just described. Chamber 52 allows the introducing of a measurement gas (mixture gas) that contains oxygen and flammable gas or nitrogen oxide gas. Reference-gas introducing chamber 54 is an enclosed space defined by solid electrolyte 34 and insulation layers 32, 36. Into the chamber 54, a reference gas such as atmospheric air can be introduced.

Oxide-containing electrode 42 and Pt electrode 44 of first oxygen pump 40 are electrically coupled via ammeter 58a and voltage source 56a. Similarly, active electrode 48 and Pt electrode 50 of second oxygen pump 46 are electrically coupled via ammeter 58b and voltage source 56b. Heater 38 is incorporated in (mounted within) insulation layer 36. The main purpose of the provision of heater 38 is to increase the temperature of solid electrolyte 34. Increasing the temperature of solid electrolyte 34 makes it easy for oxygen ions to move within corresponding solid electrolytes 34. The heating temperature of heater 38 is controlled by a controller. Heater 38 preferably contains a metal powder, such as platinum (Pt), which is highly resistant to oxidation, and a ceramic substance. Heater 38 can be appropriately selected from known heaters. As described above, first solid electrolyte 34a and second solid electrolyte 34b may be formed from a single solid electrolyte 34 or may be formed from separate solid electrolytes.

A method for measuring a gas concentration by utilizing the gas sensor will now be described. The method may be referred to as a gas constituent detection method. This assertion applies to the other embodiments of the present invention. With reference to FIG. 3, a measurement gas (mixture gas) containing oxygen and flammable gas or nitrogen oxide gas is introduced into gas detection chamber 52. Consequently, oxide-containing electrode 42 and active electrode 48 are both exposed to the measurement gas.

In this condition, a current flowing through first oxygen pump 40 is measured by ammeter 58a. As the current, a limiting current, which corresponds to the oxygen concentration before a combustion reaction of the oxygen and the flammable gas or before a reductive reaction of the nitrogen oxide gas, is measured. That is, first oxygen pump 40 functions as a limiting current type of oxygen sensor, which measures the oxygen concentration (i.e., a quantity of oxygen) before the reaction. Also, a current flowing through second oxygen pump 46 is measured by ammeter 58b. As the current, a limiting current, which corresponds to the oxygen concentration after the combustion reaction of the oxygen and the flammable gas, is measured. In other words, second oxygen pump 46 functions as a limiting current type of oxygen sensor, which measures the oxygen concentration after the reaction (i.e., a quantity of oxygen).

On the other hand in the presence of both oxygen and nitrogen oxide gas, a limiting current corresponding to the oxygen and oxygen that was produced by the reduction of the nitrogen oxide gas is measured. That is, the second oxygen pump 46 serves as a limiting current type oxygen sensor that measures the concentration of the oxygen that is present after the above mentioned gas reaction.

Then, a difference in limiting current between oxygen pumps 40, 46 is calculated. By calculating the limiting current difference, a quantity of flammable gas that had the combustion reaction with the oxygen gas or a quantity of nitrogen oxide gas that had the reductive reaction can be obtained. Accordingly, the concentration of the flammable gas or nitrogen oxide gas, which is present in the measurement gas can be obtained.

First oxygen pump 40 includes oxide-containing electrode 42 that has the characteristics (advantages), which were described above in detail. Accordingly, by utilizing the gas sensor, the concentration of the flammable gas can be measured quickly (yielding fast response) and highly accurately by the limiting current difference between oxygen pumps 40, 46. Further, the gas sensor has a chemical stability and high durability.

Fifth Detailed Representative Embodiment

Figure 4:
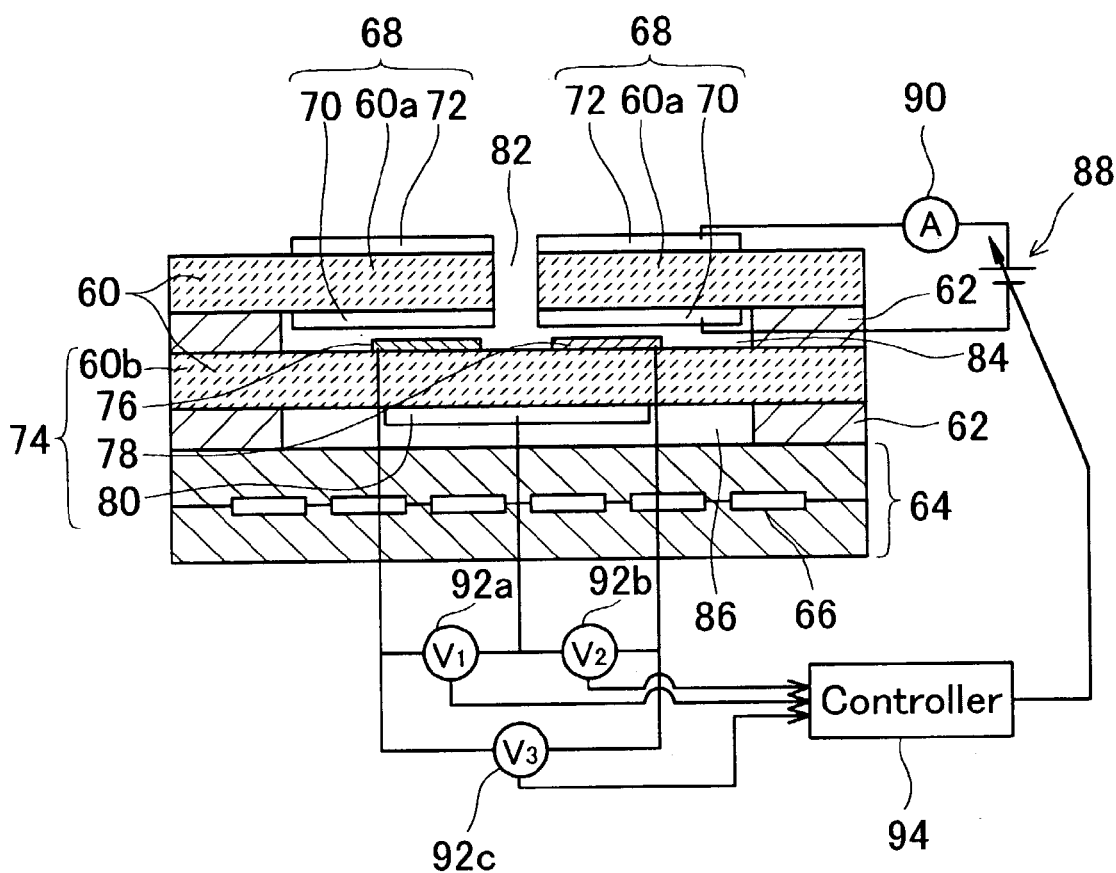
FIG. 4 is a schematic cross-sectional view of a gas sensor according to the fifth representative embodiment of the present teachings.

As shown in FIG. 4, a gas sensor according to a fifth embodiment of the present invention includes first electrochemical oxygen pump 68, a measurement element 74, insulation layers 62, 64, heater 66, voltage source 88, ammeter 90, first to third volt meters 92a to 92c, and controller 94. The measurement element 74 measures the concentration of flammable gas. First oxygen pump 68 has: first solid electrolyte 60a, which conducts oxide ions; oxide-containing electrode 70, which was described in the above illustrated embodiments; and Pt electrode 72. Oxide-containing electrode 70 is disposed on the gas detection chamber 84 side of first solid electrolyte 60a. Pt electrode 72 is disposed on the open space side of first solid electrolyte 60a.

In the fifth embodiment, the measurement element 74 is formed by the electromotive force generation element. The electromotive force generation element 74 has second solid electrolyte 60b, active electrode 76, inactive electrode 78, and reference electrode 80. The active electrode 76 is active to the combustion catalytic reaction of the flammable gas and oxygen. The inactive electrode 78 restricts a combustion catalytic reaction of the flammable gas Active electrode 76 and inactive electrode 78 are disposed on the gas detection chamber 84 side of second solid electrolyte 60b. Reference electrode 80 is disposed on the reference-gas introducing chamber 86 side of second solid electrolyte 60b. From the viewpoint on the flammable gas (in particular, hydrocarbon gas) selectivity, active electrode 76 preferably contains at least platinum (Pt), palladium (Pd), rhodium (Rh), silver (Ag), nickel (Ni), or gold (Au). Active electrode 76 preferably contains the selected constituent as the main constituent.

Inactive electrode 78 preferably restricts a catalytic reaction of the hydrocarbon gas and oxygen. Also, in the view of the hydrocarbon gas selectivity, inactive electrode 78 preferably has catalytic activity to a hydrogen gas and a carbon monoxide gas. Or inactive electrode 78 preferably has electrochemical activity to oxide ions of the oxide-ion-conductive solid electrolyte. In these aspects, because inactive electrode 78 generates potential (mixed potential) that is equal to active electrode 76, the ability to selectively detect the hydrocarbon gas is improved. Inactive electrode 78 is preferably the oxide-containing electrode that was described above in detail. Inactive electrode 78 may also contain at least one of the metallic elements Pt, Pd, Rh, Ag, Ni, and Au in order to improve responsiveness. The content of the metallic element is preferably 0.1 to 50% by mass, more preferably 0.1 to 20% by mass, to the total mass of the oxide selected from (I), the oxide selected from (II), or the mixture thereof.

Gas detection chamber 84 is an enclosed space that was defined by solid electrolyte 60, and insulation layer 62. Gas diffusion hole 82 is made in first solid electrolyte 60a. First solid electrolyte 60a functions as a diffusion control layer. Into chamber 84, a measurement gas can be introduced. The measurement gas contains oxygen and flammable gas. Another enclosed space 86 is defined by second solid electrolyte 60b and insulation layers 62, 64. Into enclosed space 86, a reference gas such as an atmospheric air can be introduced.

Oxide-containing electrode 70 and Pt electrode 72 are electrically coupled via ammeter 90 and voltage source 88. Active electrode 76 and reference electrode 80 are electrically coupled via first voltmeter 92a. Inactive electrode 78 and reference electrode 80 are electrically coupled via second voltmeter 92b. Active electrode 76 and inactive electrode 78 are electrically coupled via third voltmeter 92c. Between voltmeters 92a to 92c and voltage source 88 is controller (e.g., computer) 94, which controls the voltage of voltage source 88 based upon voltage values (electromotive force values) that were respectively measured by voltmeters 92a to 92c.

Next, a method for measuring a gas concentration by utilizing the gas sensor will be explained. First, measurement gas (mixture gas) containing flammable gas (e.g., hydrocarbon gas), which is present in open space, is introduced into gas detection chamber 84 under a predetermined diffusion resistance. Then, a voltage is applied by voltage source 88. As a result, the oxygen in the gas detection chamber 84 is ionized by an oxygen pumping action of first oxygen pump 68. The oxygen ions are expelled into the open space from gas detection chamber 84 via oxide-containing electrode 70, first solid electrolyte 60a, and Pt electrode 72. In first solid electrolyte 60a, etc, a pumping current flows in accordance with a quantity of expelled oxygen. By measuring the pumping current by ammeter 90, the quantity of expelled oxygen can be found. The quantity of oxygen that is expelled can be changed according to the voltage of voltage source 88. Therefore, the oxygen partial pressure (concentration) in gas detection chamber 84 can be controlled, by controlling the voltage of voltage source 88 by means of controller 94 based upon the electromotive force that was generated between the electrodes of electromotive force generation element 74 (e.g., between electrodes 78, 80, between electrodes 76, 80).

This way, electromotive force generation element 74 functions as not only the gas concentration measurement element but also an element that monitors the oxygen concentration. It is preferable that the oxygen concentration in gas detection chamber 84 be controlled in the above-described manner in order to accurately measure the gas concentration. However, only the oxygen may be simply expelled by first oxygen pump 68 without controlling the oxygen concentration of gas detection chamber 84. This assertion applies to the other embodiments of the present invention as well.

The flammable concentration in the measurement gas in gas detection chamber 84, in which the oxygen concentration has been controlled as described above, is measured by electromotive force generation element 74, which serves as the concentration measurement element.

When electromotive force generation element 74 is placed in the ambient atmosphere that contains the flammable gas (e.g., hydrocarbon gas), in which the oxygen concentration has been controlled, electromotive forces that correspond to the oxygen concentration differences are generated respectively between active electrode 76 and reference electrode 80, between inactive electrode 78 and reference electrode 80, and between active electrode 76 and oxide-containing electrode 78. By measuring the electromotive force generated between active electrode 76 and oxide-containing electrode 78 by use of third voltmeter 92c, the concentration of the flammable gas can be detected.

Oxide-containing electrode 78 has the characteristics (advantages) that were described above in detail. Accordingly, the gas sensor enables the concentration of the flammable gas to be measured quickly (yielding fast response) and highly accurately by the value of the electromotive force generated between active electrode 76 and oxide-containing electrode 78. Further, oxide-containing electrode 78 is chemically stable and durably excellent.

In the gas sensor, the oxygen partial pressure in gas detection chamber 84 is preferably adjusted to the range of $10^{-7}$ to $10^{-2}$ atm based upon the electromotive force generated between inactive electrode 78 and reference electrode 80. By controlling the oxygen partial pressure to such a range, the concentration of a minute quantity of flammable gas (in particular, hydrocarbon gas) can be measured with high accuracy even in an environment in which the oxygen concentration changes or in an environment in which the oxygen concentration is high.

After the burning of the flammable gas in gas detection chamber 84, the oxygen partial pressure near active electrode 76 is preferably adjusted to the range of $10^{-12}$ to $10^{-13}$ atm based upon the electromotive force generated between active electrode 76 and reference electrode 80. By controlling the oxygen concentration to such a range, a sudden oxygen concentration decrease due to the burning of the flammable gas and the oxygen near active electrode 76 can be avoided. As a result, gas detection chamber 84 retains a large quantity of oxygen at all times. Therefore, inactive electrode 78, which is an oxide-containing electrode of the fifth embodiment, restricts the reductive reaction of the electrode. In addition, the electromotive force is stably generated by electromotive force generation element 74 over a wide concentration range. Accordingly, the concentration of the flammable gas (in particular, hydrocarbon gas) can be accurately measured over the wide concentration range.

Sixth Detailed Representative Embodiment

Figure 5:
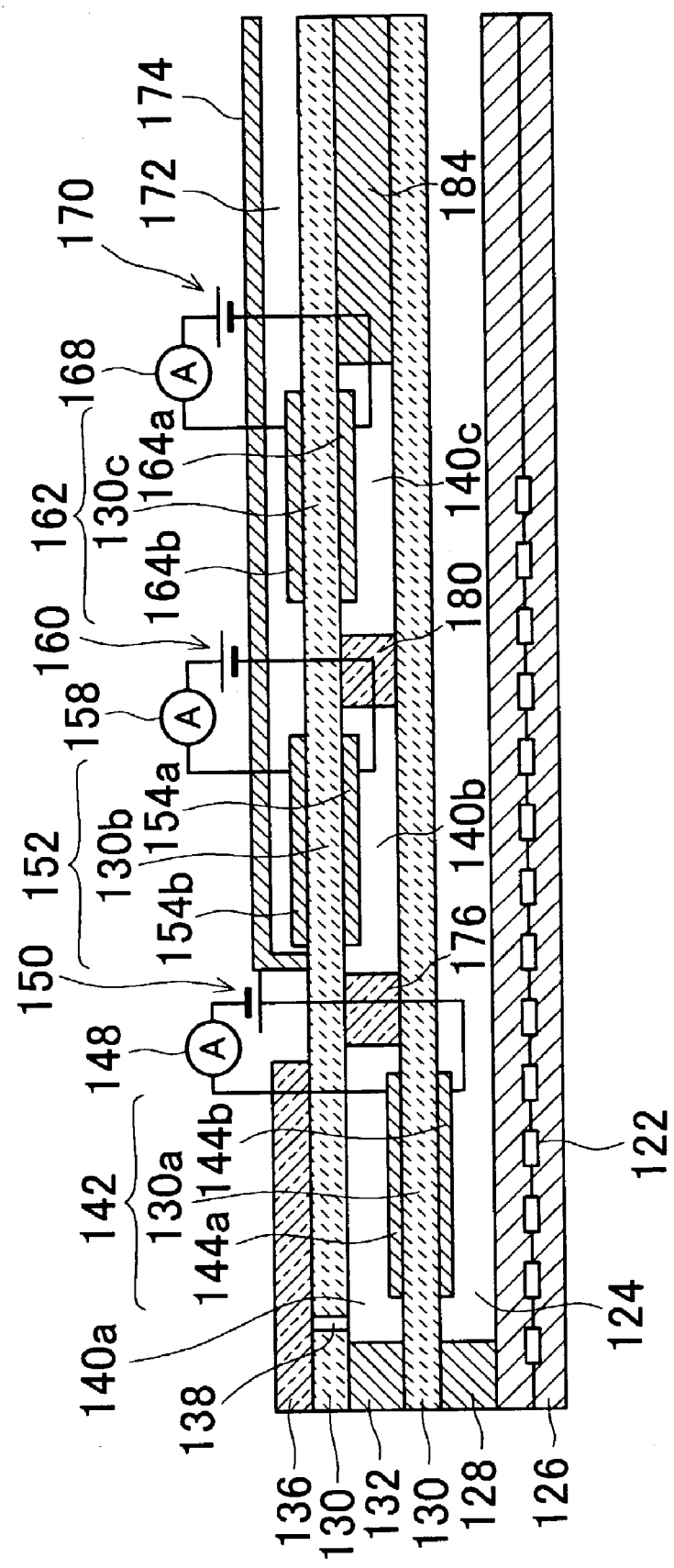
FIG. 5 is a schematic cross-sectional view of a gas sensor according to the sixth representative embodiment of the present teachings.

As shown in FIG. 5, a gas sensor according to the sixth embodiment of the present invention includes: first oxygen pump 142; flammable gas measurement element (second oxygen pump) 152; a nitrogen oxide gas measurement element (third oxygen pump) 162. The gas sensor further includes detecting device 148, 158, 168, diffusion control layer 136, 176, 180, exciting device 150, 160, 170, heater 122, and insulation layers 126, 128, 132, 174, 184, etc.

First oxygen pump 142 has first solid electrolyte 130a that is oxide-ion conductive, and a pair of first electrodes 144a, 144b. The pair of first electrodes 144a, 144b are disposed on respectively the upper side and lower side of first solid electrolyte 130a. First solid electrolyte 130a is part of walls that define first chamber 140a. Herein, the walls defining first chamber 140a are: part of upper solid electrolyte layer 130; part of lower solid electrolyte layer 130 (including first solid electrolyte 130a); and insulation layer 132 and second diffusion control layer 176. Of the walls, upper solid electrolyte layer 130 has gas introducing hole 138.

One of the pair of first electrodes, 144a, is disposed on the first chamber 140a side (upper side) of first solid electrolyte 130. First electrode 144a is called "first inside electrode". The other of the pair of first electrodes, 144b, is disposed on the lower passage 124 side (lower side) of first solid electrolyte 130. Lower passage 124 communicates with atmospheric air. The other first electrode, 144b, is called "first outside electrode". First diffusion control layer 136 is formed in contact with part of solid electrolyte layer 130. First diffusion control layer 136 and gas diffusion hole 138 are disposed next to each other. First ammeter 148, which serves as first detecting device, and first voltage source 150, which serves as first energizing device, are coupled in series between the pair of first electrodes 144a, 144b.

Second oxygen pump 152, which functions as a flammable gas measurement element, includes second solid electrolyte 130b that is oxide-ion conductive, and a pair of second electrodes 154a, 154b. The pair of second electrode 154a, 154b are disposed in contact with the upper side and lower side, respectively, of second solid electrolyte 130b. Second solid electrolyte 130b forms part of walls that define second chamber 140b. Herein, the walls defining second chamber 140b are: part of upper solid electrolyte layer 130 (including second solid electrolyte 130b); part of lower solid electrolyte layer 130; and second diffusion control layer 176 and third diffusion control layer 180.

One of the pair of second electrodes, 154a, is disposed on the second chamber 140b side (lower side) of second solid electrolyte 130b. The second electrode 154a is called "second inside electrode". The other of the pair of electrodes, 154b, is disposed on the upper passage 172 side (upper side) of second solid electrolyte 130b. Upper passage 172 communicates with the atmospheric air. The other second electrode 154b is called "second outside electrode". Second diffusion control layer 176 is disposed between first chamber 140a and second chamber 140b. Second ammeter 158, which serves as second detecting device, and second voltage source 160, which serves as second energizing device, are coupled in series between second electrodes 154a, 154b.

Third oxygen pump 162, which functions as a nitrogen oxide gas measurement element, includes: third solid electrolyte 130c that is oxide-ion conductive, and a pair of third electrodes 164a, 164b. The pair of third electrodes 164a, 164b are disposed in contact with the lower side and upper side, respectively, of third electrolyte 130c. Third electrolyte 130c forms part of walls that define third chamber 140c. Herein, the walls defining third chamber 140c are: part of upper solid electrolyte layer 130 (including third solid electrolyte 130c); part of lower solid electrolyte layer 130; and third diffusion control layer 180 and insulation layer 184.

One of the pair of third electrodes, 164a, is disposed on the third chamber 140c side (lower side) of third solid electrolyte 130c. The third electrolyte 164a is called "third inside electrode". The other of the pair of third electrodes, 164b, is disposed on the upper passage 172 side (upper side) of third solid electrolyte 130c. Upper passage 172 communicates with the atmospheric air. The other third electrode 164b is called "third outside electrode". Third diffusion control layer 180 is disposed between second chamber 140b and third chamber 140c. Third ammeter 168, which is third detecting device, and third voltage source 170, which is third energizing device, are coupled in series between the pair of third electrodes 164a, 164b.

Below lower solid electrolyte layer 130 is lower insulation layer 126 via lower atmospheric air communication passage 124 and insulation layer 128. Lower insulation layer 126 has heater 122 embedded in it. Above upper solid electrolyte layer 130 is upper insulating layer 174 via upper atmospheric air communication passage 172. However, upper insulation layer 174 does not extend above part of upper solid electrolyte layer 130, which part corresponds to first oxygen pump 142.

Second inside electrode 154a of second oxygen pump 152 preferably has high activity to flammable gas and low activity to nitrogen oxide gas. Second inside electrode 154a preferably contains gold (Au) or an alloy that includes Au. Specifically, second inside electrode 154a preferably contains not only Au, but also at least platinum (Pt), palladium (Pd), rhodium (Rh), silver (Ag), or nickel (Ni) from the viewpoint on the flammable gas (in particular, hydrocarbon gas) selectivity. Especially, a cermet electrode (hereinafter called "Pt—Au electrode") that contains a ceramic substance and an alloy comprising Pt—Au is more preferable.

It is preferable for third inside electrode 164a of third oxygen pump 162 to include at least Pt, Pd, Rh, Ag, or Ni from the viewpoint on the nitrogen oxide gas selectivity. It is more preferable that third inside electrode 164a be a cermet electrode (hereinafter called "Pt—Pd electrode") that includes a Pt—Pd alloy and a ceramic substance, a cermet electrode (hereinafter called "Pt—Au—Pd electrode") that contains a Pt—Au—Pd alloy and a ceramic substance, a cermet electrode (hereinafter called "Pt—Rh electrode") that includes a Pt—Rh alloy and a ceramic substance, and a cermet electrode (hereinafter called "Pt—Rh—Pd electrode") that includes a Pt—Rh—Pd alloy and a ceramic substance.

In the Pt—Pd alloy, Pt—Au—Pd alloy, or Pt—Rh—Pd alloy, which forms part of third inside electrode, a quantity of Pd that is added to Pt (=100×Pd/(Pt+Pd)) is preferably 1% or more by mass. If the quantity of Pd added to Pt is 1% or more by mass, the activity of third inside electrode 164a to $NO_X$ can be increased. In order to impart the activity that is equal to or higher than that of Pt electrode, the quantity of Pd that is added to Pt is preferably 90% or less by mass, more preferably 5 to 40% by mass.

In the case where third inside electrode 164a includes the Pt—Au—Pd alloy, the weight ratio of Pd to Au (hereinafter referred to as Pd/Au ratio) is preferable 1.67 or more. In the case, activity to a $NO_X$ gas can improve in comparison to the Pt—Au electrode that contains no Pd. In addition, if the Pd/Au ratio is 1.67 or more, the electrode that is nearly equal to Pt electrode in activity to the $NO_X$ gas can be obtained. Also, in the case where third inside electrode 164a partly includes the Pt—Rh—Pd alloy, if a quantity of Rh exceeds 30 wt %, an electrode resistance increases. Therefore, it is preferable that the quantity of Rh be 30 wt % or less.

The materials of outside electrodes 144b, 154b, 164b are not limited in particular. These electrodes 144b, 154b, 164b each may be an electrode that contains at least, for example, Pt, Pd, Rh, Ag, Ni, or Au. A cermet electrode (Pt electrode) that contains Pt and a ceramic substance may be utilized.

The ceramic substance that partly constitutes each of the above-described electrodes 144, 154, 164) is added in order to increase adhesion between the electrodes and the corresponding solid electrolytes or in order to decrease electrode reaction resistances. The composition of the ceramic substance and a quantity of ceramic substance can be arbitrarily selected as long as satisfactory adhesion is assured between the electrodes and the corresponding solid electrolytes. If a quantity of ceramic substance is large, the conductivity of the electrodes decreases. Normally, the aforementioned electrodes each contain approximately 5 to 20% by mass of the ceramic substance that has the same composition as the corresponding solid electrolyte.

A method for measuring a gas concentration by utilizing the gas sensor will now be discussed. First, the gas sensor (specifically, the gas diffusion hole 138 and the perimeter of first diffusion control layer 136 disposed above gas diffusion hole 138) is exposed to measurement gas (i.e., mixture gas) that contains oxygen, flammable gas, and nitrogen oxide gas. The measurement gas is gradually introduced into first chamber 140a through gas diffusion hole 138 under a predetermined diffusion resistance, which is regulated by first diffusion control layer 136.

While the measurement gas has been introduced in first chamber 140a, a voltage is applied by first voltage source 150 so that first inside electrode 144a becomes a cathode and first outside electrode 144b becomes an anode. Consequently, the oxygen pumping action of first oxygen pump 142 causes the oxygen to be expelled into the lower atmospheric air communication passage 124 via first inside electrode 144a, first solid electrolyte 130a, and first outside electrode 144b in that order. A pumping current (limiting current) that is flowing at the case is measured by first ammeter 148. Thus, the concentration of the oxygen gas in the measurement gas can be accurately measured.

In the sixth embodiment, first inside electrode 144a of first oxygen pump 142 is the oxide-containing electrode that was discussed above. The oxide-containing electrode has high activity to the oxygen gas and low activity to the flammable gas and the nitrogen oxide gas. Even if the voltage that is applied to first oxygen pump 142 is high, the activity to the nitrogen oxide gas scarcely increases. Further, because oxide-containing electrode 144a is low in resistant to the electrode reaction that accompanies the oxygen ionization, a large quantity of oxygen can be pumped by the application of a low voltage. In addition, fast response can be yielded. Accordingly, first oxygen pump 142 having oxide-containing electrode 144a has the high ability to pump oxygen. Moreover, first oxygen pump 142 is chemically stable and highly durable.

Even if the measurement gas contains the flammable gas and the nitrogen oxide gas, first oxygen pump 142 is capable of minimizing influence upon these gases and selectively decreasing the oxygen that is present in the measurement gas. This makes it possible to introduce into second chamber 140b the measurement gas which contains the almost the same quantities of flammable gas and nitrogen oxide gas that were originally present in the measurement gas and in which the sufficient quantity of oxygen has been selectively decreased.

The measurement gas in which the oxygen gas has been selectively reduced within first chamber 140a by first oxygen pump 142 is gradually introduced to second chamber 140b through second diffusion control layer 176. While the measurement gas is introduced to second chamber 140b, a voltage is applied by second voltage source 160 so that second inside electrode 154a becomes a cathode and second outside electrode 154b becomes an anode. Consequently, the oxygen pumping action of second oxygen pump 152 causes oxygen to be introduced into second chamber 140b from upper atmospheric air communication passage 172 through second outside electrode 154b, second solid electrolyte 130b, and second inside electrode 154a in that order.

Normally, the oxygen is pumped through the cathode, the solid electrolyte, and the anode. However, in the sixth embodiment, a reverse voltage is generated by a large difference in oxygen concentration between second inside electrode 154a and second outside electrode 154b. Therefore, the oxygen is pumped through the anode, the solid electrolyte, and a cathode in that order.

As described above, second chamber 140b accommodates the measurement gas which contains almost the same quantity of flammable gas that was originally present in the measurement gas. Furthermore, in the measurement gas, the oxygen gas that is combustion-reactive to the flammable gas has been selectively and sufficiently reduced. Therefore, a quantity of oxygen that is pumped by second oxygen pump 152 is close to a quantity of oxygen that is required for the burning of the flammable gas whose quantity has unchanged in the measurement gas. At this case, a pumping current that flows in second oxygen pump 152 is measured by second ammeter 158. Thus, the flammable gas concentration in the measurement gas can be measured highly accurately and rapidly (yielding a fast response).

In the sixth embodiment, because second inside electrode 154a of second oxygen pump 152, contains Au or an alloy comprising Au, electrode 154a has high activity to the flammable gas and low activity to the nitrogen oxide gas. Accordingly, by utilizing second oxygen pump 152, the oxygen introduced by the pumping action of pump element 152 and the flammable gas introduced to second chamber 140b can be burned with little effect exerted upon the nitrogen oxide gas. This makes it possible to introduce into third chamber 140c the measurement gas which contains almost the same quantity of nitrogen oxide gas that was originally present in the measurement gas and in which the oxygen gas and the flammable gas have been sufficiently reduced.

The measurement gas, after the flammable gas was burned in second chamber 140b, is gradually introduced into third chamber 140c through third diffusion control layer 180. While the measurement gas has been introduced into third chamber 140c, a voltage is applied by third voltage source 170 so that third inside electrode 164a becomes a cathode and third outside electrode 164b becomes an anode. Consequently, the nitrogen oxide gas in the measurement gas is decomposed. The oxygen pumping action of third oxygen pump 162 causes the oxygen, which was produced by the decomposition, to be expelled from third chamber 140c into upper atmospheric air communication passage 172 via third inside electrode 164a, third solid electrolyte 130c, and third outside electrode 164b in that order.

As described above, third chamber 140c accommodates the measurement gas which contains the nitrogen oxide gas whose quantity has hardly unchanged in the measurement gas. Furthermore, in the measurement gas, the oxygen gas and the flammable gas have been reduced. Therefore, a quantity of oxygen that is pumped out by third oxygen pump 162 is approximate to a quantity of the oxygen that was produced by the decomposition of the same quantity of the nitrogen oxide gas that was originally present in the measurement gas. At this case, a pumping current that flows in third oxygen pump 162 is measured by third ammeter 168. Thus, the nitrogen oxide gas concentration in the measurement gas can be measured rapidly (yielding a fast response) and highly accurately.

According to the sixth embodiment, if the measurement gas contains the oxygen gas, the flammable gas, and the nitrogen oxide gas, the concentrations of these gases are selectively and highly accurately detected at the same time. The devices for measuring only flammable gas concentration or the device for measuring only a nitrogen gas concentration have been known. However, a device for selectively measuring the flammable gas concentration and the nitrogen oxide concentration with high accuracy has not previously been contemplated. The gas sensor of the sixth embodiment can selectively measure the oxygen gas concentration, the flammable gas concentration, and the nitrogen oxide gas concentration highly accurately. It was difficult to realize such a useful, valuable device.

When exhaust gas that comes out of, e.g., a vehicle is measured as measurement gas, the oxygen concentration in the measurement gas may be high or may greatly vary depending on a running state of the vehicle. However, in the sixth embodiment, the high oxygen pumping action of first oxygen pump 142 sufficiently reduces in advance the oxygen contained in the measurement gas. Therefore, even if the oxygen gas concentration in the measurement gas is high or varies, the flammable gas concentration or the nitrogen gas concentration can be measured with high accuracy.

Further, when exhaust gas as from a vehicle is measured as measurement gas, flammable gas or nitrogen oxide gas that are present in the measurement gas may be low in concentration or very small in quantity. However, in the sixth embodiment, the high oxygen pumping action of first oxygen pump 142 sufficiently reduces in advance the oxygen contained in the measurement gas. And, the effect of the first oxygen pump 142 upon the flammable gas and nitrogen oxide gas is very little. Accordingly, even if the flammable gas and the nitrogen oxide gas have low concentrations or small quantities, the concentrations of theses gases can be measured highly accurately.

The gas sensor can be utilized in various fields as a matter of course. In particular, the gas sensor is very useful in the field of automobile industry in order to reduce quantities of flammable gas and nitrogen oxide gas in an exhaust gas, which is a big problem that the field has to deal with, and in order to control a quantity of these gases with high accuracy.

Seventh Detailed Representative Embodiment

Figure 6:
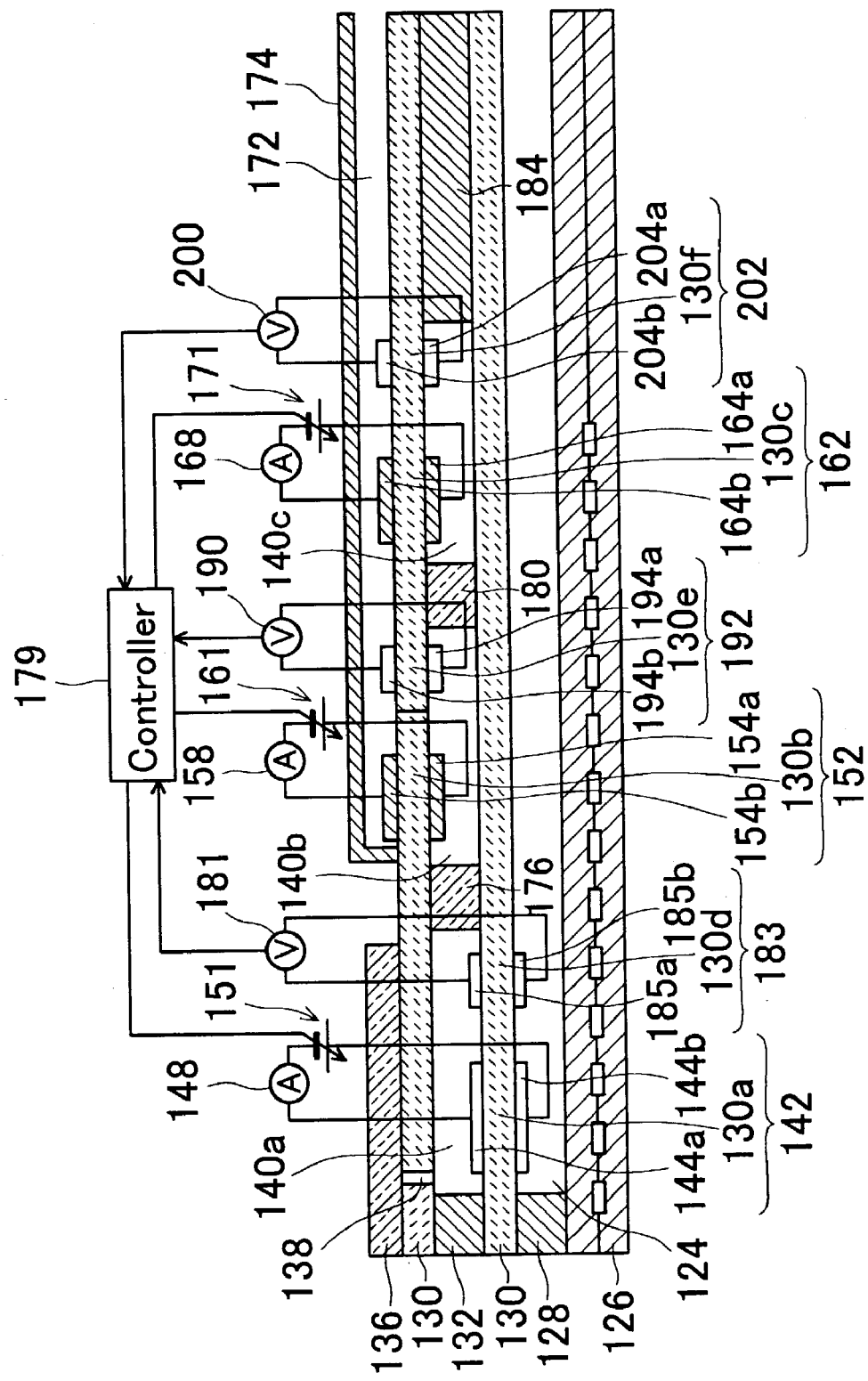
FIG. 6 is a schematic cross-sectional view of a gas sensor according to the seventh embodiment of the present teachings.

A gas sensor according to the seventh embodiment of the present invention is depicted in FIG. 6. In the gas sensor, voltages that applied to oxygen pumps 142, 152, 162, respectively, are controlled in accordance with the oxygen partial pressures in corresponding chamber parts 140a, 140b, 140c.

Specifically, in addition to the structure that is the same as the structure of the gas sensor of the sixth embodiment, the gas sensor of the seventh embodiment includes electromotive force generation element 183, 192, 202, all of which may be called "electromotive force detection cells". In addition, the gas sensor includes voltmeter 181, 190, 200, and controller 179. First electromotive force generation element 183 has solid electrolyte 130d and a pair of first controlling electrodes 185a, 185b. Second electromotive force generation element 192 has solid electrolyte 130e and a pair of second controlling electrodes 194a, 194b. Third electromotive force generation element 202 has solid electrolyte 130f and a pair of second controlling electrodes 204a, 204b. Voltmeter 181 is coupled between controlling electrodes 185a, 185b. Voltmeter 190 is coupled between controlling electrodes 194a, 194b. Voltmeter 200 is coupled between controlling electrodes 204a, 204b. Controller 179 is coupled between voltmeters 181, 190, 200 and corresponding voltage sources 151, 161, 171.

As in the case of first inside electrode 144a, one of the first controlling electrodes, 185a, preferably includes the oxide-containing electrode, which was discussed above, in order to prevent influence upon flammable gas and nitrogen gas that are present in measurement gas. As in the case of second inside electrode 154a, one of the second controlling electrodes, 194a, preferably includes an electrode (e.g., Pt—Au electrode) that contains Au or an alloy comprising Au, in order to prevent influence upon the nitrogen oxide gas. The other controlling electrodes 185b, 194b, 204a, 204b are not limited in particular and may include, e.g. Pt electrode.

Next, a method for measuring a gas concentration by utilizing the gas sensor will be explained. As in the case of the first embodiment, while measurement gas that contains oxygen, flammable gas, and nitrogen oxide gas is introduced in first chamber 140a, a voltage is applied between first electrodes 144a, 144b by first voltage source 151. In this case, an electromotive force is generated between first controlling electrodes 185a, 185b in accordance with a difference in oxygen concentration between the ambient atmosphere in first chamber 140a and the atmospheric air (reference air) in lower atmospheric air communication passage 124. The voltage is measured by first voltmeter 181, and the voltage data is transmitted to controller 179. Oxygen partial pressure in first chamber 140a is found from the voltage. In accordance with the voltage, the voltage (of first voltage source 151) that is applied between first electrodes 144a, 144b is controlled so that the oxygen partial pressure in first chamber 140a reaches a desired value.

While the measurement gas is introduced in second chamber 140b, a voltage is applied between second electrodes 154a, 154b by second voltage source 161. In this case, an electromotive force is generated between second controlling electrodes 194a, 194b in accordance with a difference in oxygen concentration between the ambient atmosphere in second chamber 140b and the atmospheric air in upper external communication passage 172. The voltage is measured by second voltmeter 190, and the voltage data is transmitted to controller 179. Oxygen partial pressure in second chamber 140b is found from the voltage. In accordance with the voltage, the voltage (of second voltage source 161) that is applied between second electrodes 154a, 154b is controlled so that the oxygen partial pressure in second chamber 140b reaches a desired value. Optionally, the oxygen concentration in the gas introduced in second chamber 140b can be controlled by utilizing the voltage value measured by second voltmeter 190 and by controlling the voltage that is applied to first oxygen pump 142.

Further, while the measurement gas is introduced in third chamber 140c, a voltage is applied between third electrodes 164a, 164b by third voltage source 171. In this case, an electromotive force is generated between third controlling electrodes 204a, 204b in accordance with a difference in oxygen concentration between the ambient atmosphere in third chamber 140c and atmospheric air in upper external communication passage 172. The voltage is measured by third voltmeter 200, and the voltage data is transmitted to controller 179. From the voltage, oxygen partial pressure in third chamber 140c is found and, therefore, the voltage that is applied between third electrodes 164a, 164b can be controlled.

Also, because the concentration of the oxygen remaining in third chamber 140c is found, a concentration signal that is obtained from third oxygen pump 162 can be corrected. In addition, a quantity of remaining oxygen can be obtained by utilizing, as third control electrode 204a, an electrode that contains Au or an alloy comprising Au, by coupling a power source and an ammeter to third electromotive force generation element 202, by expelling only the oxygen from third chamber 140c, and by measuring a current flowing at this time. By utilizing this current value, a current corresponding to the oxygen can be removed from the currents flowing through third oxygen pump 162. Accordingly, the accuracy of the nitrogen oxide gas concentration measurement improves.

This gas sensor allows the voltage value to be controlled by various methods. For example, by exerting control such that the oxygen partial pressure in first chamber 140a has a desired constant value, the measurement gas in first chamber 140a, which has the constant oxygen partial pressure, can be introduced into second chamber 140b. Accordingly, the flammable gas or nitrogen oxide gas concentration can be measured with high accuracy even if the oxygen partial pressure of the measurement gas greatly fluctuates. In this case, it is preferable for the oxygen partial pressure to be decreased to the lowest value possible in order to prevent the flammable gas or nitrogen oxide gas concentration measurement accuracy from degrading due to the presence of the oxygen that was introduced from first chamber 140a to second chamber 140b or to third chamber 140c. It is preferable for the oxygen partial pressure to control less than or equal to $10^{-5}$ atom.

In addition, for example, the voltage that is applied by second voltage source 161 is preferably controlled by controller 179 such that the second chamber 140b receives the sufficient quantity of oxygen that is required for the burning of the flammable gas of the measurement gas in second chamber 140b. Controlling the voltage in such a manner improves the accuracy of the measurement of the flammable gas concentration that is obtained from the pumping current of second oxygen pump 152 (i.e. the pumping current indicates a quantity of oxygen gas introduced in second chamber 140b).

In order to improve the flammable gas or nitrogen oxide gas concentration measurement accuracy, the oxygen partial pressure in chamber parts 140a, 140b, 140c are preferably low. It is preferable for voltage sources 151, 161, 171 to be controlled by appropriately selected electromotive force generation elements 183, 192, 202, voltmeters 181, 190, 200, and controller 179.

As exemplified by the gas sensors of the above embodiments, the gas sensors according to the present invention preferably include a diffusion control portion that introduces measurement gas into at least any one of the chambers under the predetermined diffusion resistance. By including the diffusion control portion, a limiting current characteristic that serves as an indicator for a quantity of expelled or introduced oxygen can be obtained for each pump element.

In particular, the diffusion control portion is preferably disposed in front of the first chamber. The diffusion control portions may be provided in front of the second chamber and the third chamber separately. Preferably, the gas sensors of the present invention further include a device (typically, ammeter and voltmeter) for measuring the current flowing through or the electromotive force generating in at least one of the oxygen pump.

Preferably, the gas sensors further include an energizing device that supplies power to the pair of electrodes of at least any one of the oxygen pumps. Specifically, it is preferable that the gas sensors include an energizing device that supplies power to the pair of electrodes of the oxygen pump in order to expel from the predetermined chamber an oxygen gas that is present in the measurement gas introduced in the predetermined chamber. It is preferable that the gas sensors include an energizing device that supplies power to the pair of electrodes of the oxygen pump in order to introduce oxygen required to burn the flammable gas that is present in the measurement gas introduced in the predetermined chamber. It is preferable that the gas sensors include an energizing device that supplies power to the pair of electrodes of the oxygen pump in order to decompose nitrogen oxide gas that is present in the measurement gas introduced in the predetermined chamber, and in order to expel the oxygen, a decomposition product, from the predetermined chamber.

Preferably, the gas sensors according to the present invention further include a heating section that heats at least any one of the oxygen pump. By increasing the temperature of the solid electrolyte by means of the heating section, the oxygen pumping action of the solid electrolyte can be exerted sufficiently. In addition, it is preferable that the gas sensors according to the present invention further include an oxygen concentration monitor device for monitoring the oxygen concentration in any one of the chamber parts. Preferably, the gas sensors of the present invention further includes a control device for controlling a quantity of power that is supplied to the oxygen pump in accordance with the oxygen concentration that was monitored by the oxygen concentration monitor. The provision of such oxygen concentration monitor device and control device further improves the gas measurement accuracy.

In the above described fifth embodiment, the flammable gas measurement element was exemplified by the electromotive force generation element 74. In the above described sixth and seventh embodiments, the flammable gas measurement element and the nitrogen oxide gas measurement element were exemplified by the second oxygen pump 152 and the third oxygen pump 162, respectively. However, these measurement element may be constructed of another known gas measurement elements or the like. The known gas measurement elements are not limited in particular and may be selected suitably. For example, a resistance type of gas measurement element, which uses semiconductor, another electromotive force sensor, current sensor, etc, or a catalytic combustion type of gas concentration measurement element can be selected.

In the sixth and seventh embodiments, the pumping current that flows in first oxygen pump 142 is measured by first ammeter 148, thereby measuring a quantity of expelled oxygen gas, and the quantity is regarded as the concentration of the oxygen gas contained in the measurement gas. However, without such an oxygen gas concentration measurement, only the flammable gas and nitrogen oxide gas concentrations may be measured.

In the sixth and seventh embodiment, the nitrogen oxide gas concentration measurement is not absolutely necessary and, therefore, third oxygen pump 162 may not be included. In such a case, the above described gas sensor is utilized as a device that selectively measures the oxygen gas concentration and the flammable gas concentration or as a device that measures the flammable gas concentration. In this case, if the nitrogen oxide gas is not present in the measurement gas, second inside electrode 154a of second oxygen pump 152 may not contain Au that weakens activity to the nitrogen oxide gas. Such second inside electrode 154a is preferably formed from an electrode that contains at least, e.g., Pt, Pd, Rh, Ag, or Ni. For instance, a Pt electrode is preferable.

In the sixth and seventh embodiments, the measurement of the flammable gas concentration is not absolutely requisite. In this case, third oxygen pump 162 may be eliminated and second oxygen pump 152 may measure the nitrogen oxide gas concentration. In such a case, second inside electrode 154a of second oxygen pump 152 needs to be highly active to the nitrogen oxygen gas. Therefore, preferably second inside electrode 154a contains no Au. Desirably, second inside electrode 154a may be formed from an electrode that contains at least, e.g., Pt, Pd, Rh, Ag, or Ni. For instance, the Pt electrode is preferable.

In the sixth and seventh embodiments, the gas concentrations are measured by measuring the pumping currents flowing through corresponding oxygen pumps 142, 152, 162 by means of corresponding ammeters 148, 158, 168. However, the gas concentrations may also be measured such that the electromotive forces, generated due to oxygen concentration differences between the pair of electrodes of corresponding oxygen pumps 142, 152, 162, are measured by the corresponding voltmeters.

In the above described sixth and seventh embodiments, second chamber 140b and third chamber 140c are separated by third diffusion control layer 180. However, second chamber 140b and third chamber 140c may be connected integrally. In this case, the flammable gas concentration and the nitrogen oxide gas concentration are measured in the substantially single chamber.

In the sixth and seventh embodiments, in order to selectively measure the concentration of, in particular, a hydrocarbon gas, which is flammable gas, a catalyst may be added into, e.g., the diffusion control layer. By virtue of the catalyst, $H_2$ gas, CO gas, etc are selectively burned and removed in advance.

Formation of Oxide-Containing Electrodes of the First Embodiment

The electrodes labeled 1 to 30, which are shown in Table 3 below, were formed.

TABLE 3

| Electrode Number | Electrode Material | Resistance Ratio |
|---|---|---|
| 1 | $Ce_{0.8}Sm_{0.2}O_{2-\alpha}$ | 1.0 |
| 2 | $Ce_{0.8}Pr_{0.2}O_{2-\alpha}$ | 2.1 |
| 3 | $Pr_{0.6}Sr_{0.4}MnO_{3-\alpha}$ | 0.6 |
| 4 | $La_{0.6}Sr_{0.4}MnO_{3-\alpha}$ | 0.8 |
| 5 | $La_{0.8}Sr_{0.2}CrO_{3-\alpha}$ | — |
| 6 | $SrTi_{0.6}Fe_{0.4}O_{3-\alpha}$ | 5.2 |
| 7 | $La_{0.8}Ca_{0.2}CoO_{3-\alpha}$ | — |
| 8 | $Ce_{0.9}Ca_{0.1}O_{2-\alpha}$ | 0.9 |
| 9 | $Ce_{0.8}Gd_{0.2}O_{2-\alpha}$ | 1.2 |
| 10 | $La_{0.6}Sr_{0.4}Co_{0.95}Ni_{0.05}O_{3-\alpha}$ | 0.6 |
| 11 | $Pr_{0.6}Sr_{0.4}Mn_{0.95}Ni_{0.05}O_{3-\alpha}$ | 0.5 |
| 12 | 25% by mass of $Pr_{0.6}Sr_{0.4}MnO_{3-\alpha}$ + 75% by mass of $Ce_{0.8}Sm_{0.2}O_{2-\alpha}$ | 0.15 |
| 13 | 50% by mass of $Pr_{0.6}Sr_{0.4}MnO_{3-\alpha}$ + 50% by mass of $Ce_{0.8}Sm_{0.2}O_{2-\alpha}$ | 0.04 |

TABLE 3-continued

| Electrode Number | Electrode Material | Resistance Ratio |
|---|---|---|
| 14 | 75% by mass of $Pr_{0.6}Sr_{0.4}MnO_{3-\alpha}$ + 25% by mass of $Ce_{0.8}Sm_{0.2}O_{2-\alpha}$ | 0.1 |
| 15 | 50% by mass of $Pr_{0.8}Sr_{0.2}MnO_{3-\alpha}$ + 50% by mass of $Ce_{0.8}Sm_{0.2}O_{2-\alpha}$ | 0.05 |
| 16 | 50% by mass of $La_{0.8}Sr_{0.2}CrO_{3-\alpha}$ + 50% by mass of $Ce_{0.8}Sm_{0.2}O_{2-\alpha}$ | 0.25 |
| 17 | 50% by mass of $La_{0.8}Sr_{0.2}MnO_{3-\alpha}$ + 50% by mass of $Ce_{0.8}Pr_{0.2}O_{2-\alpha}$ | 0.1 |
| 18 | 50% by mass of $Pr_{0.6}Sr_{0.4}Mn_{0.95}Ni_{0.05}O_{3-\alpha}$ + 50% by mass of $Ce_{0.6}Sm_{0.2}O_{2-\alpha}$ | 0.04 |
| 19 | 50% by mass of $La_{0.6}Sr_{0.4}Co_{0.95}Ni_{0.05}O_{3-\alpha}$ + 50% by mass of $Ce_{0.8}Sm_{0.2}O_{2-\alpha}$ | 0.1 |
| 20 | Layered Body Formed from $[Ce_{0.8}Sm_{0.2}O_{2-\alpha}]$ and $[Pr_{0.6}Sr_{0.4}MnO_{3-\alpha}]$ | 0.05 |
| 21 | Layered Body Formed from [25% by mass of $Pr_{0.6}Sr_{0.4}MnO_{3-\alpha}$ + 75% by mass of $Ce_{0.8}Sm_{0.2}O_{2-\alpha}$] and [50% by mass of $Pr_{0.6}Sr_{0.4}MnO_{3-\alpha}$ + 50% by mass of $Ce_{0.8}Sm_{0.2}O_{2-\alpha}$] | 0.11 |
| 22 | Layered Body Formed from $[Ce_{0.8}Sm_{0.2}O_{2-\alpha}]$ and [50% by mass of $Pr_{0.6}Sr_{0.4}MnO_{3-\alpha}$ + 50% by mass of $Ce_{0.8}Sm_{0.2}O_{2-\alpha}$] | 0.1 |
| 23 | Layered Body Formed from $[Ce_{0.8}Sm_{0.2}O_{2-\alpha}]$ and [50% by mass of $Pr_{0.8}Sr_{0.2}MnO_{3-\alpha}$ + 50% by mass of $Ce_{0.8}Sm_{0.2}O_{2-\alpha}$] | 0.06 |
| 24 | Layered Body Formed from $[Ce_{0.9}Ca_{0.1}O_{2-\alpha}]$ and $[Pr_{0.6}Sr_{0.4}MnO_{3-\alpha}]$ | 0.05 |
| 25 | Layered Body Formed from $[Ce_{0.8}Sm_{0.2}O_{2-\alpha}]$ and $[La_{0.6}Sr_{0.4}Co_{0.95}Ni_{0.05}O_{3-\alpha}]$ | 0.08 |
| 26 | 90% by mass of $SrTi_{0.6}Fe_{0.4}O_{3-\alpha}$ + 9.8% by mass of Pt + 0.2% by mass of Au | 1.51 |
| 27 | 45% by mass of $La_{0.6}Sr_{0.4}CrO_{3-\alpha}$ + 45% by mass of $Ce_{0.8}Sm_{0.2}O_{2-\alpha}$ + 9.8% by mass of Pt + 0.2% by mass of Au | 0.02 |
| 28 | 45% by mass of $La_{0.8}Sr_{0.2}CrO_{3-\alpha}$ + 45% by mass of $Ce_{0.8}Sm_{0.2}O_{2-\alpha}$ + 10% by mass of YSZ | 0.18 |
| 29 | 88% by mass of Pt + 2% by mass of Au + 10% by mass of YSZ | — |
| 30 | 90% by mass of Pt + 10% by mass of YSZ | — |

Each of the electrodes that are distinguished by the electrode numbers 1 to 28, which are shown in Table 3, was formed in the following manner. First, various metal oxides were mixed with ether at a predetermined mass ratio. The mixture were then dried and baked as 1200° C. Thereafter, ether that contains 5% by mass of cellulose was added to the baked mixture such that the solid content was 70% by mass. Subsequently, the resulting mixture was kneaded by a roll mill in order to prepare printing paste A. Next, printing paste A was screen printed on a particular sheet. Then, this sheet was dried and baked at approximately 1500° C. Thus, the electrodes were each formed. These electrodes exemplify the oxide-containing electrodes of the above described first embodiment. These electrodes are preferable to be utilized as electrodes 8 of the second embodiment (refer to FIG. 1), as electrodes 22 of the third embodiment (refer to FIG. 2), as electrode 42 of the fourth embodiment (refer to FIG. 3), as electrodes 70, 78 of the fifth embodiments (refer to FIG. 4), and as first inside electrodes 144a of the sixth and seventh embodiments (refer to FIGS. 5 and 6, respectively).

In order to form the electrode labeled electrode number 29 in Table 3, Pt, Au, and YSZ (zirconia that was stabilized by 6 mol % of $Y_2O_3$) were mixed at a ratio of 88:2:10. The mixture was pasted in the same manner as the above described manner in order to prepare printing paste B. The paste B was processed in the same manner as paste A and, thus, the electrode of electrode number 29 was formed. Hereinafter, the electrode formed from the paste B, which is distinguished by electrode number 29, will be called "Pt—Au electrode". This electrode is preferable to be utilized as second inside electrodes 154a of the sixth and seventh embodiments (refer to FIGS. 5 and 6, respectively).

Further, in order to form the electrode labeled electrode number 30 in Table 3, YSZ (zirconia that was stabilized by 6 mol % of $Y_2O_3$) and Pt were mixed at a ratio of 9:1. The mixture was pasted in the same manner as the above described manner in order to prepare printing paste C. Paste C was processed in the same manner as paste A and, thus, the electrode of electrode number 30 was obtained. Hereinafter the electrode that was formed from paste C will be called "Pt electrode". This electrode is preferable to be utilized as electrodes 10 of the second embodiment (refer to FIG. 1), as electrodes 24 of the third embodiment (refer to FIG. 2), as electrodes 44, 48, 50 of the fourth embodiment (refer to FIG. 3), as electrodes 72, 76, 80 of the fifth embodiment (refer to FIG. 4), and as third inside electrodes 164a and outside electrodes 144b, 154b, 164b of the sixth and seventh embodiments (refer to FIGS. 5 and 6, respectively).

(1) Formation and Evaluations of Sample Elements

Figure 7:
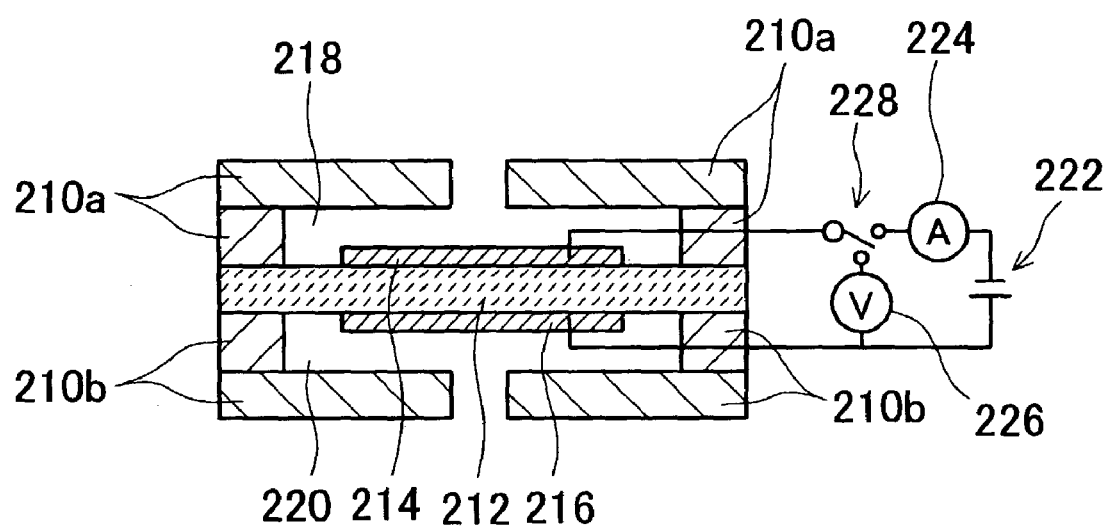
FIG. 7 is a schematic cross-sectional view of each of sample elements.

The sample element, which is shown in FIG. 7, is formed in the following manner and the performances of the electrodes in Table 3 were evaluated. In this example, the sample element was utilized as the oxygen pump. First, as the solid electrolyte that is oxide ion conductive, green sheet 212 of zirconia that was stabilized by 6 mol % of $Y_2O_3$ was prepared. Then, printing past A that was obtained by using $Ce_{0.8}Sm_{0.2}O_{2-\alpha}$ of electrode number 1 in Table 3 was screen printed on one of the sides (i.e., upper side) of green sheet 212. In addition, above described printing paste C was screen printed on the other side (i.e., lower side) of green sheet 212. After dried, green sheet 212 was baked at approximately at 1500° C. and thus electrodes 214, 216 were formed. After baking, electrodes 214, 216 were coupled via voltage source 222, ammeter 224, voltmeter 226, and switch 228, as shown in FIG. 7. Also, diffusion control bodies 210a, 210b, each of which is formed from an alumina green sheet, were attached to green sheet 212 so as define separate chambers 218, 220 with green sheet 212 disposed therebetween. Thus, sample element [1] was obtained. Hereinafter, the number given to each of the sample elements corresponds to the electrode number given to electrode 214 that is formed on one of the sides (i.e., upper side) of green sheet 212.

Also, by using $Pr_{0.6}Sr_{0.4}MnO_{3-\alpha}$ (simple body) of electrode number [3] in Table 3, electrode sample element [3] was prepared in the same manner as sample element [1]. In addition, by using a mixture of 50% by mass of $Pr_{0.6}Sr_{0.4}MnO_{3-\alpha}$ and 50% by mass of $Ce_{0.8}Sm_{0.2}O_{2-\alpha}$ of electrode number [13] in Table 3, sample element [13] was obtained in the same manner as sample element [1].

Resistance decrease effects of sample element [1] (an example of $CeO_2$ series oxide), sample element [3] (an example of perovskite oxide), and sample element [13] (an example of the mixture thereof) were evaluated. It is preferable for the electrochemical oxygen pump to expel or introduce a large quantity of oxygen in a short time. In order to achieve this, it is desirable that the resistance of each element be as low as possible. The resistance of each element consists of an electrolyte resistance and an electrode reaction resistance that accompanies a gas reaction. The electrolyte resistance is very low in comparison with the electrode reaction resistance. Accordingly, the electrode reaction resistance may be regarded as the resistance of the element.

Figure 8:
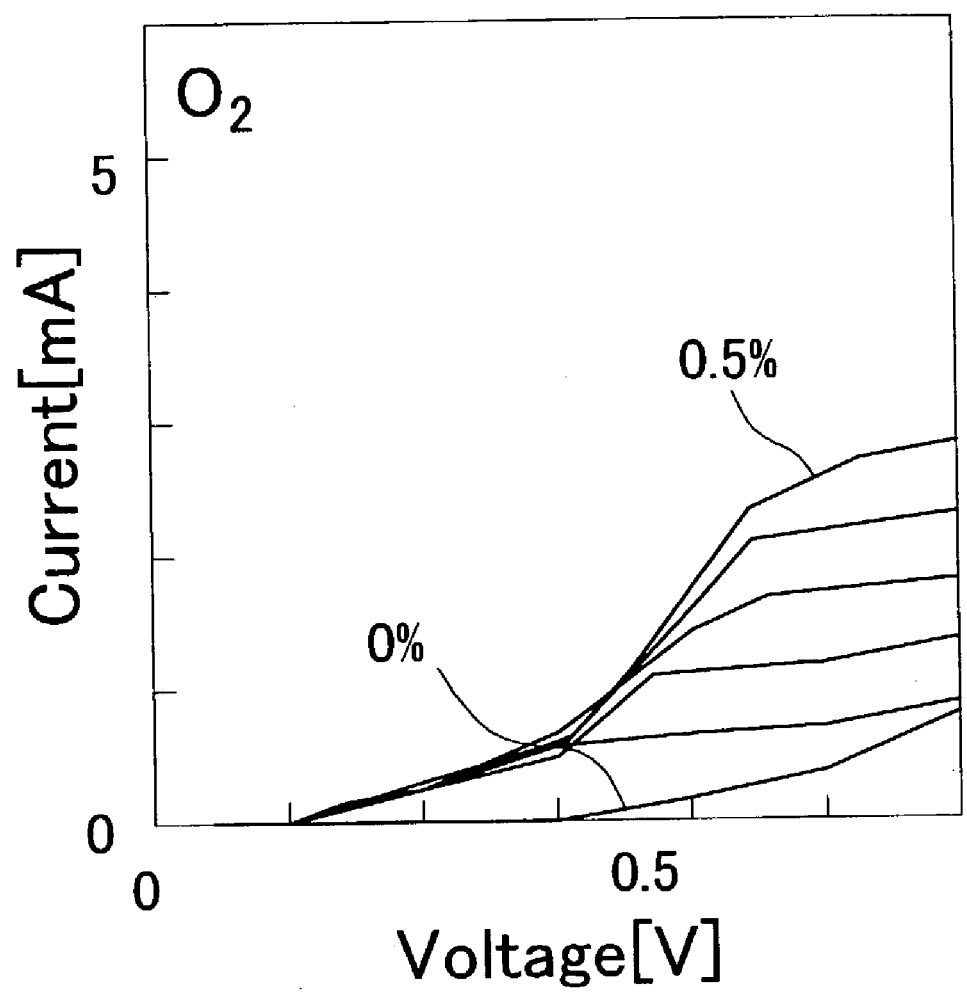
FIG. 8 is a graph showing the current—voltage characteristic of sample element [1] when the oxygen concentration is changed.
Figure 9:
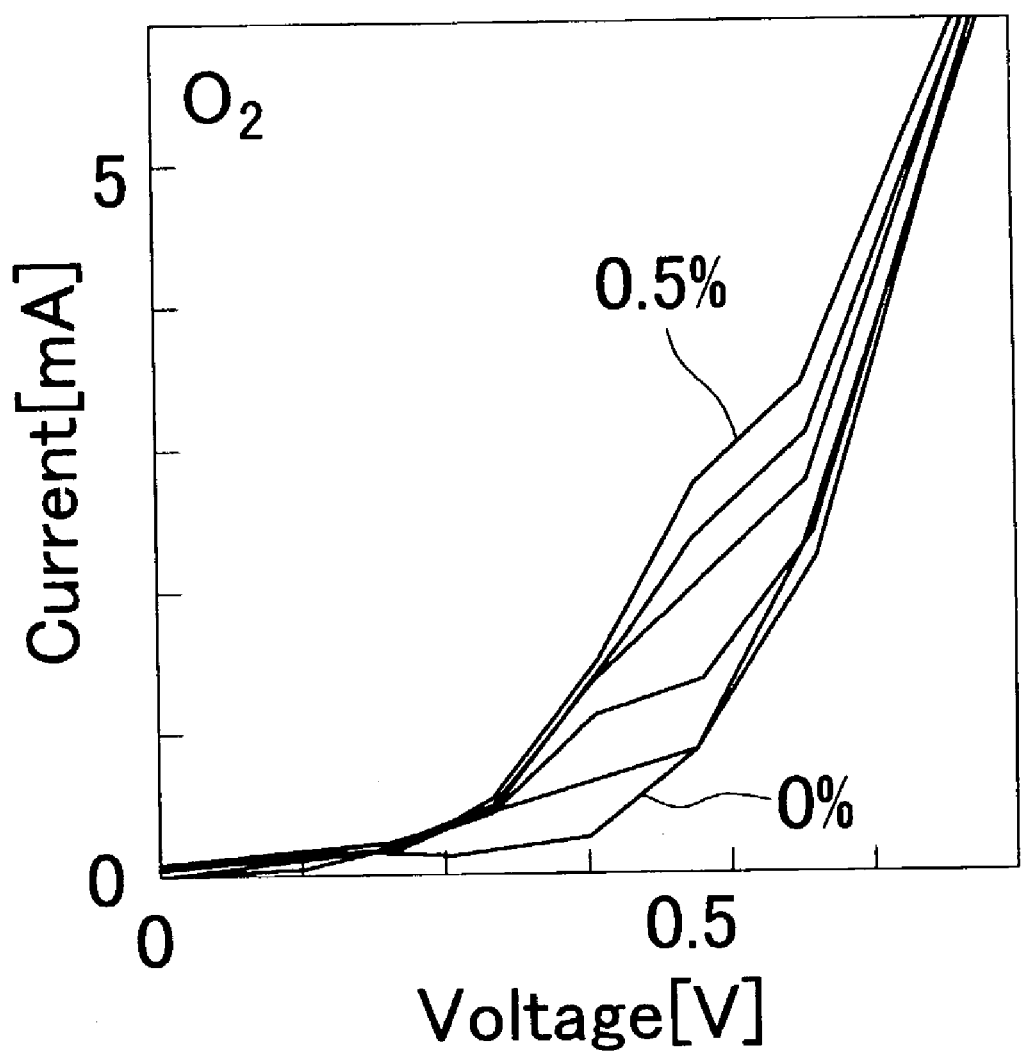
FIG. 9 is a graph showing the current—voltage characteristic of sample element [3] when the oxygen concentration is changed.
Figure 10:
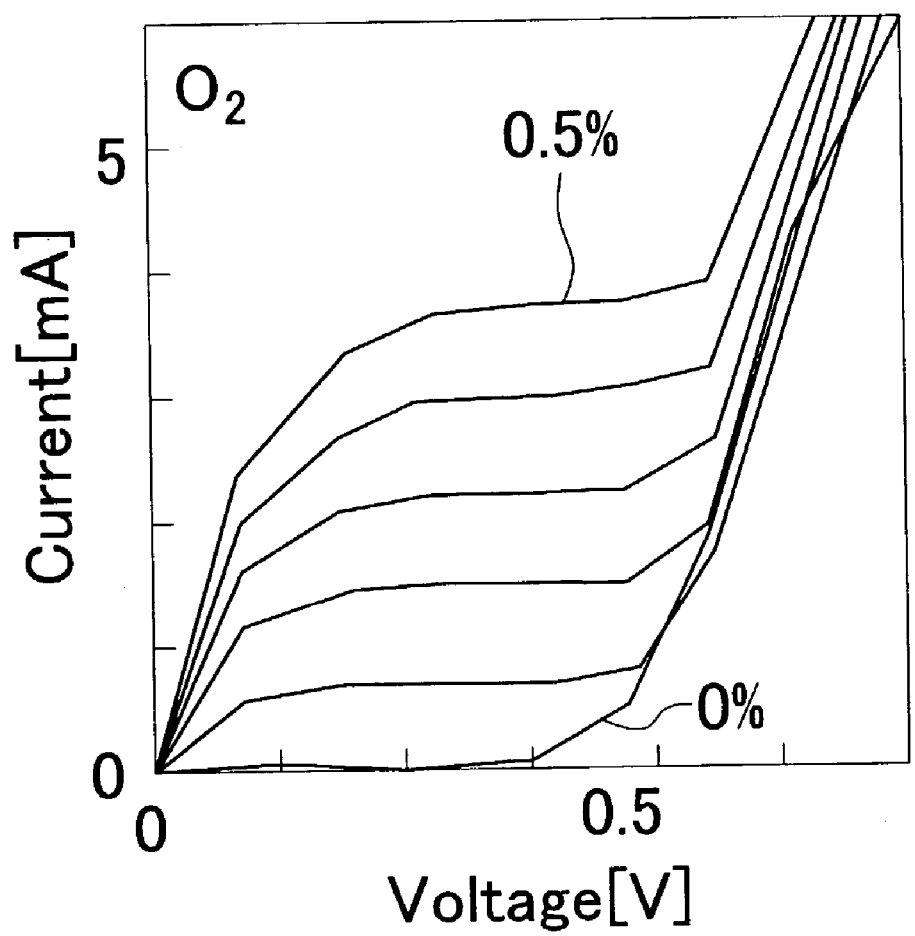
FIG. 10 is a graph showing the current—voltage characteristic of sample element [13] when the oxygen concentration is changed.

Sample elements [1], [3], [13] were evaluated. Sample elements [1], [3], [13] were heated to about 750° C. in an electric furnace, and the current—voltage characteristics (IV characteristics) of sample elements [1], [3], [13], when the oxygen concentration was changed in the range of 0 to 0.5%, were measured. FIGS. 8, 9, and 10 show the IV characteristics of sample elements [1], [3], [13], respectively.

As shown in FIGS. 8, 9, and 10, the gradients of the IV characteristics of sample elements [1], [3], [13] are all steep and, therefore, the resistances of the elements are low. In particular, in sample element [13] that includes the mixture electrode, the inclination of IV curve is steep and the resistance is very low compared to the resistances of sample elements [1], [3]. The resistance of mixture electrode sample element [13] decreased by one or more digits when the oxygen concentration was 0.5%.

Figure 11:
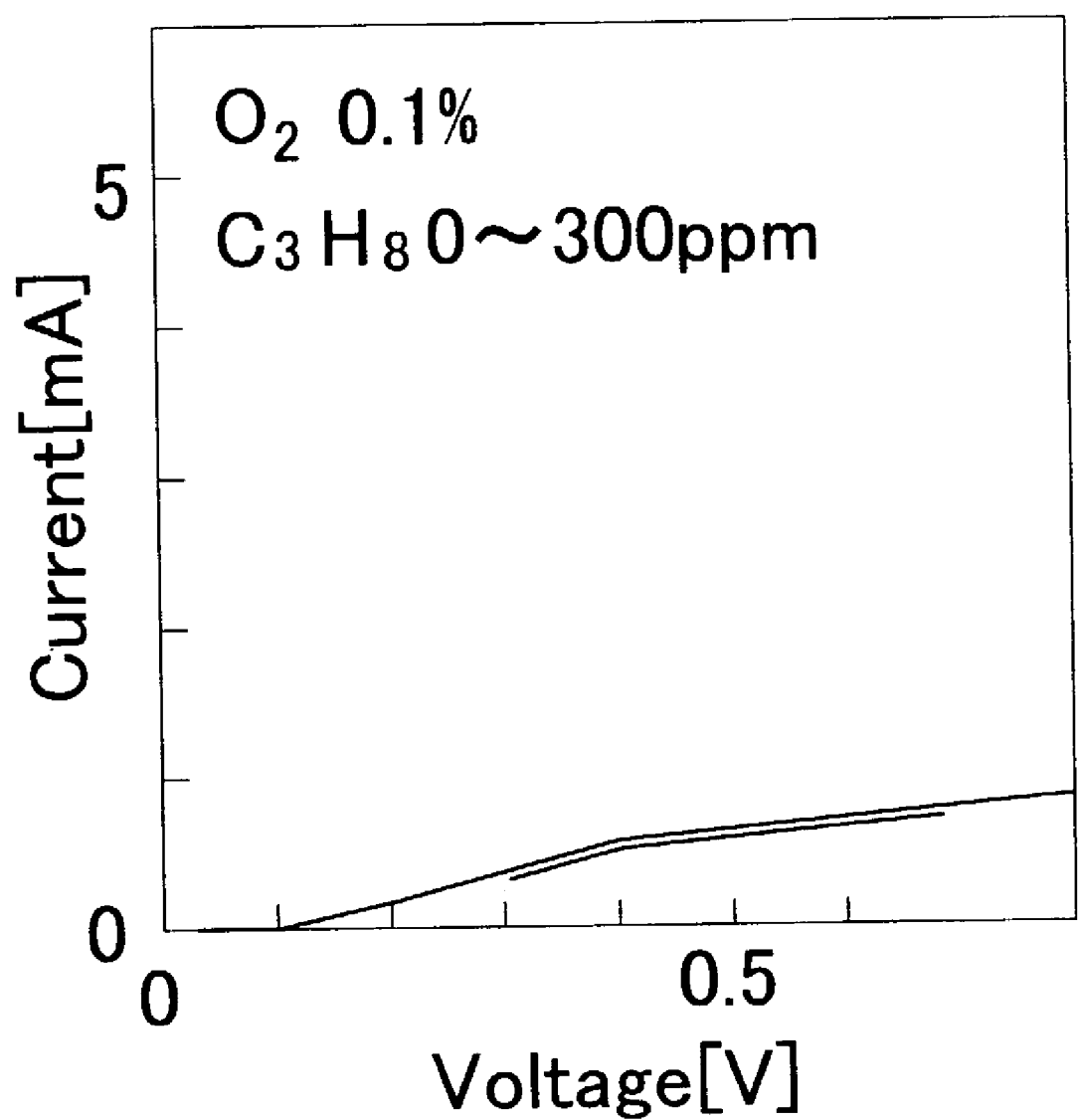
FIG. 11 is a graph showing the current—voltage characteristic of sample element [1] when flammable gas was added to an oxygen atmosphere.
Figure 12:
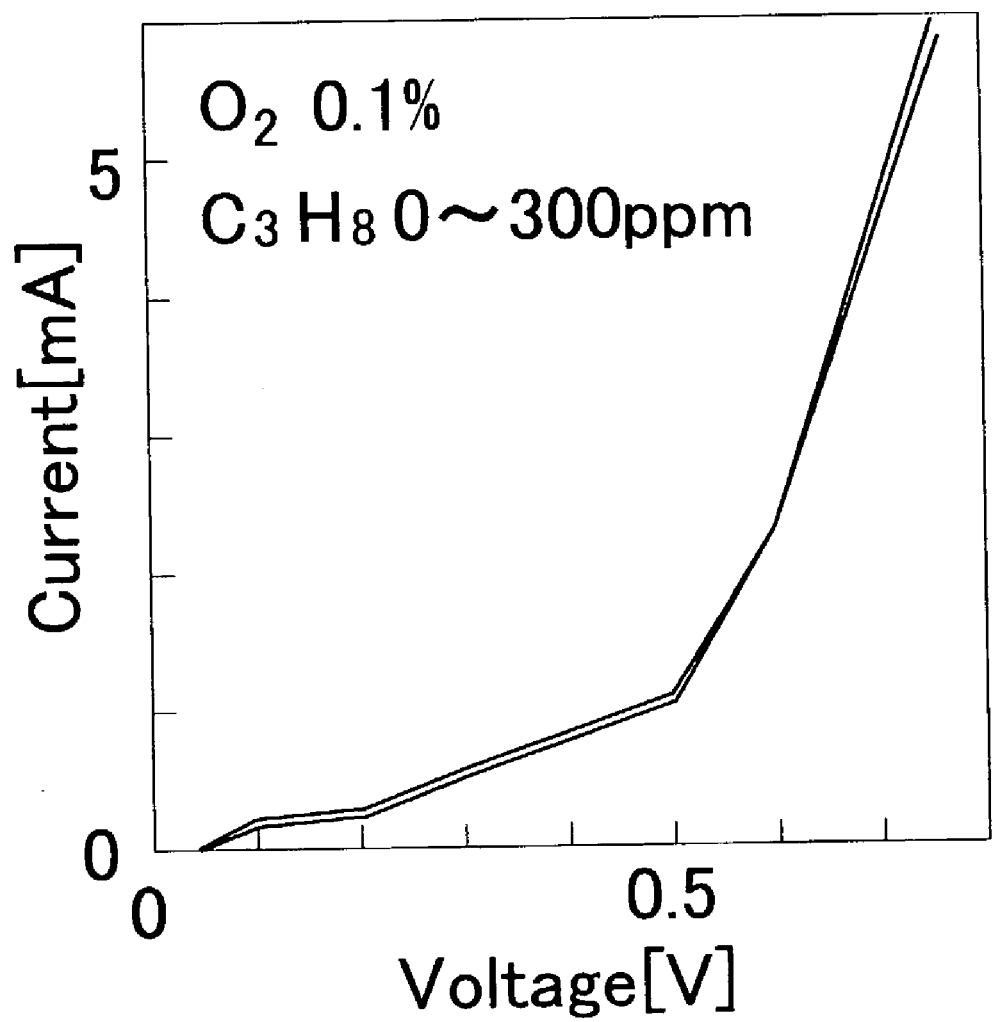
FIG. 12 is graph showing the current—voltage characteristic of sample element [3] when the same flammable gas as in FIG. 11 was added to an oxygen atmosphere.
Figure 13:
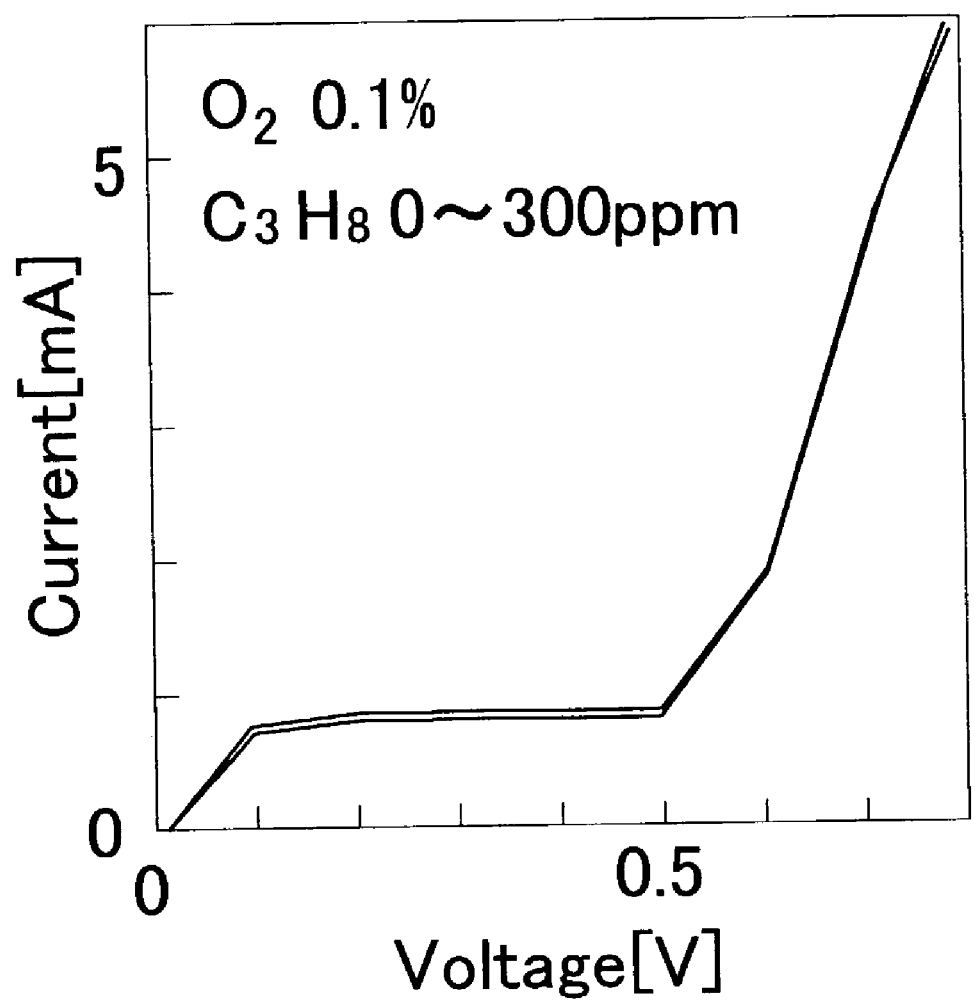
FIG. 13 is graph showing the current—voltage characteristic of sample element [13] when the same flammable gas as in FIG. 11 was added to an oxygen atmosphere.

Next, a reaction between the flammable gas and the oxygen was tested on the surface of each sample element [1], [3], [13]. The current—voltage characteristic (IV characteristic) of each sample element, when 0 to 300 ppm of $C_3H_8$ flammable gas was added to an approximately 0.1% oxygen atmosphere at about 750° C., was measured. A change in limiting current obtained at the time was evaluated. The limiting current varies according to the oxygen concentration. If the flammable gas and the oxygen react at the electrode, the oxygen concentration decreases only by the quantity that was used in the reaction and consequently the limiting currents also decreases. FIGS. 11, 12, and 13 show the IV characteristics of sample elements [1], [3], [13], respectively.

As is clear from FIGS. 11, 12, and 13, the limiting currents did not change in sample elements [1], [3], [13] despite the addition of $C_3H_8$. The results indicate that the reactions between $C_3H_8$ and the oxygen scarcely occurred at the electrodes. Such tendencies were also exhibited in the sample elements fabricated from the electrodes labeled electrode numbers [1] to [28] in Table 3. In particular, in the electrode that contains a $CeO_2$ series oxide, resistance of the element was low and the flammable gas and the oxygen hardly reacted, so that the limiting current did not decrease. The same result was obtained even in the electrode that was fabricated by bonding together layers of $CeO_2$ series oxides of different contents. The above evaluations showed that utilizing the oxide-containing electrodes of the above illustrated embodiments (in particular, the electrode that includes the mixture of perovskite oxide and the $CeO_2$ series oxide) realizes the electrochemical oxygen pump that greatly reduces the resistance of the element and selectively expels or introduces a large quantity of oxygen even in the ambient atmosphere that contains flammable gas and oxygen.

(2) Formation and Evaluations of Sample Elements

In addition to the above described sample element [13], by using $SrTi_{0.6}Fe_{0.4}O_{3-\alpha}$ (simple body) of electrode number 6 in Table 3, sample element [6] was prepared in the same manner as sample element [13]. In addition, in the same manner as sample element [13], sample element [21] was formed by using a layered body, electrode number [21] in Table 3. The layered body was formed by bonding together a layer of a mixture of 25% by mass of $Pr_{0.6}Sr_{0.4}MnO_{3-\alpha}$ and 75% by mass of $Ce_{0.8}Sm_{0.2}O_{2-\alpha}$ and a layer of a mixture of 50% by mass of $Pr_{0.6}Sr_{0.4}MnO_{3-\alpha}$ and 50% by mass of $Ce_{0.8}Sm_{0.2}O_{2-\alpha}$. In this example, the sample elements were utilized as the electromotive force generation elements.

Figure 14:
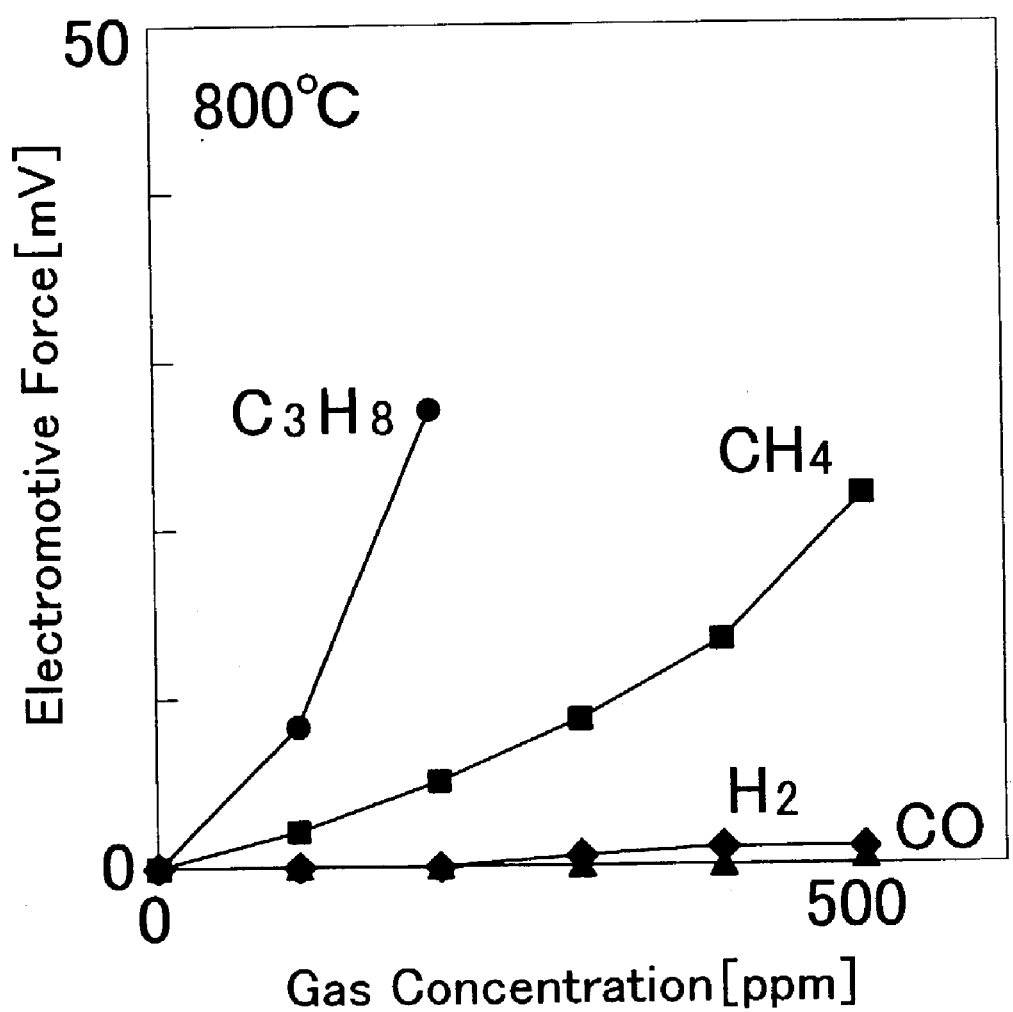
FIG. 14 is a graph showing a relationship between the concentration of each of flammable gas and the electromotive force in sample element [6].
Figure 15:
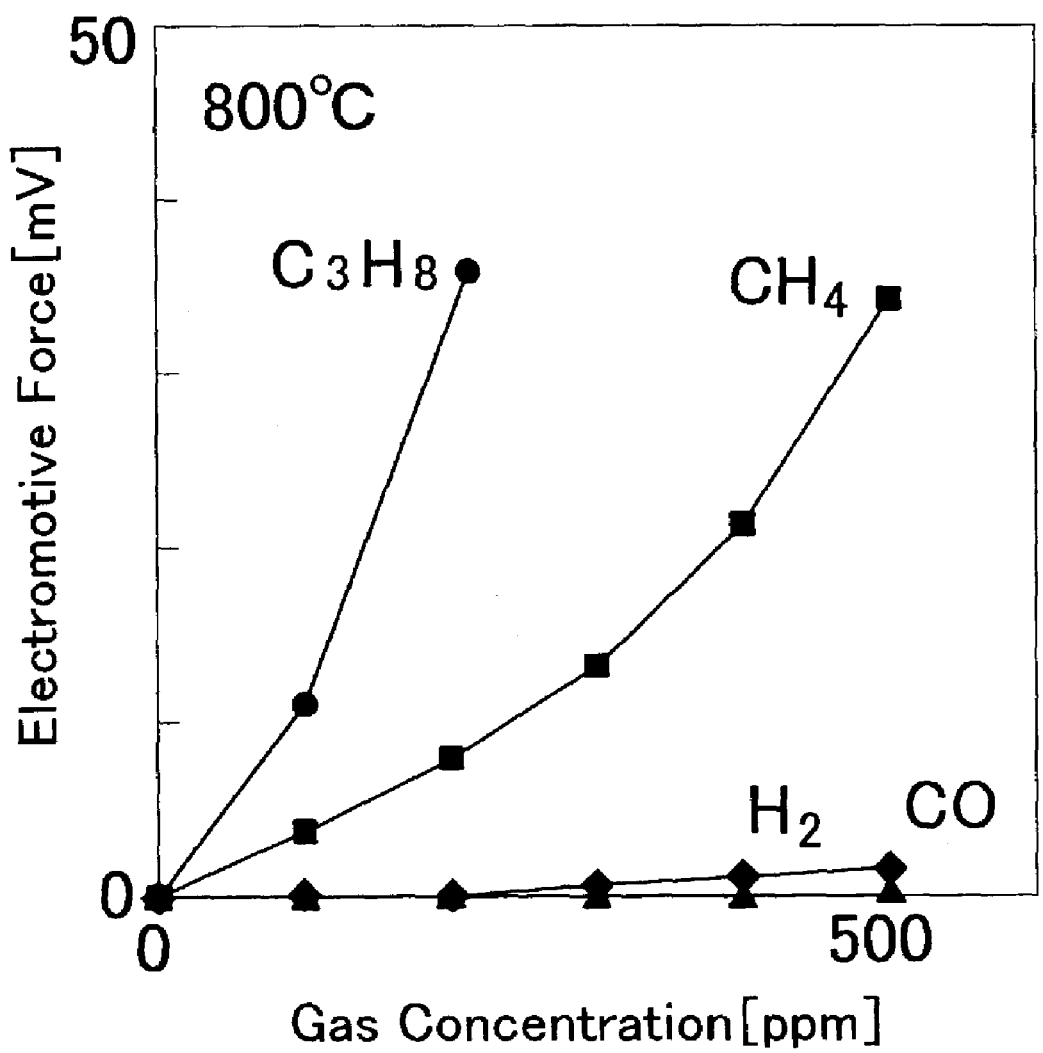
FIG. 15 is a graph showing a relationship between the concentration of each of the flammable gas, which were the same as the gases in FIG. 14, and the electromotive force in sample element [13].
Figure 16:
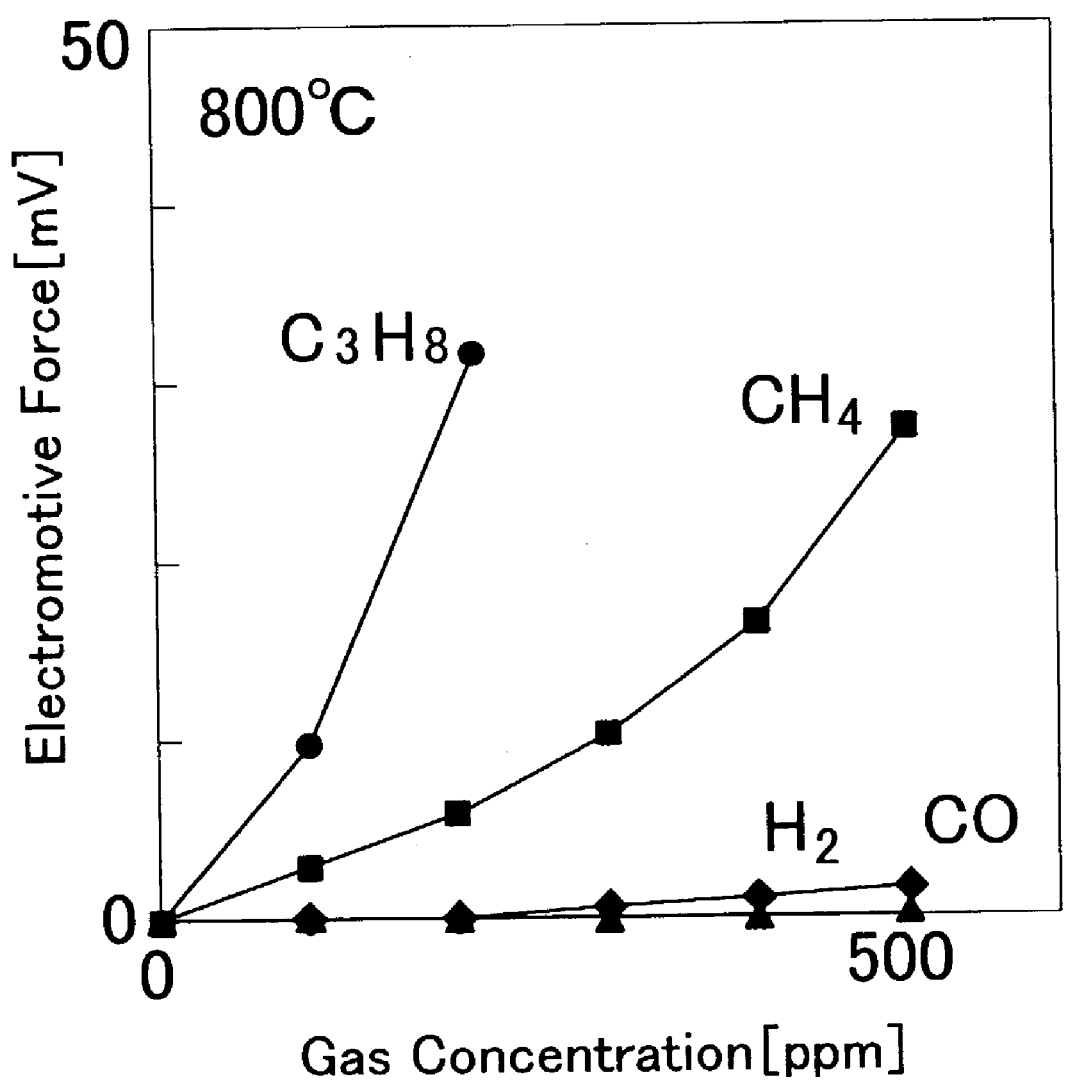
FIG. 16 is a graph showing a relationship between the concentration of each of the flammable gas, which were the same as the gases in FIG. 14, and the electromotive force in sample element [21].

Gas detection characteristics of sample elements [6], [13], [21] that function as electromotive force generation elements were tested. Specifically, each sample element [6], [13], [21] was heated (to 700 to 850° C.) in an electric furnace, and an electromotive force generated between inactive electrode 214 and active electrode 216 (refer to FIG. 7), when 0 to 500 ppm of the flammable gas ($C_3H_8$, $CH_4$, $H_2$, CO) was added to an approximately 0.1% oxygen atmosphere, was measured. FIGS. 14, 15, and 16 respectively show the relationships between the flammable gas concentrations and electromotive forces of sample elements [6], [13], [21].

As is clear from FIGS. 14, 15, and 16, in each sample element [6], [13], [21], the electromotive forces corresponding to the $C_3H_8$ concentration and the $CH_4$ concentration were selectively obtained. In particular, when $C_3H_8$ exceeded 300 ppm, 700 mV or higher electromotive force was generated. This is because the $C_3H_8$ gas in the ambient atmosphere became excessive and consequently the oxygen concentration near active electrode 216 extremely decreased. On the other hand, the electromotive forces corresponding to the $H_2$ gas and the CO gas were hardly generated. That is because a change in the potential of inactive electrode 214, which had accompanied the mixture reaction, substantially coincided with a change in the potential of active electrode 216, which had accompanied the combustion. These evaluations resulted in the discovery that the oxide-containing electrodes of the above illustrated embodiments (especially, the electrode that includes conductive perovskite oxide) is the inactive electrode that satisfactorily selectively detects hydrocarbons.

(3) Formation and Evaluations of Sample Elements

Figure 17:
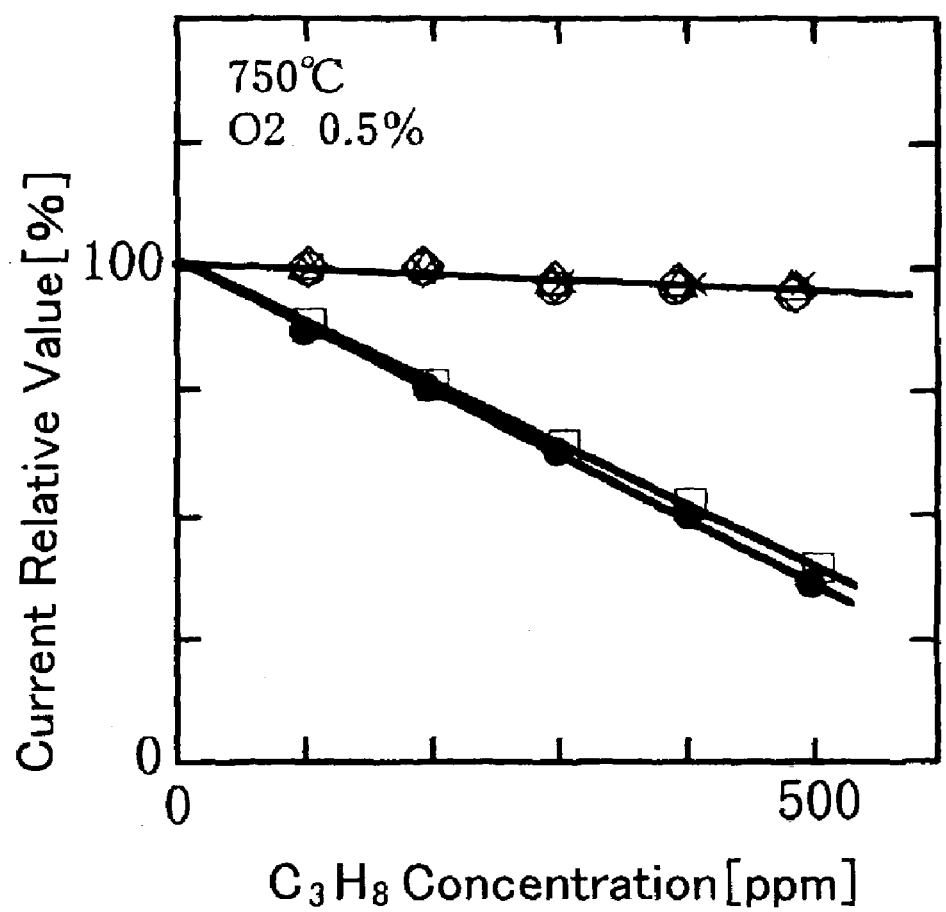
FIG. 17 is a graph showing a relationship between limiting current and the $C_3H_8$ concentration in each of sample elements [1], [13], [20], [22], [29], and [30] when the flammable gas ($C_3H_8$) was added to an oxygen atmosphere.
Figure 18:
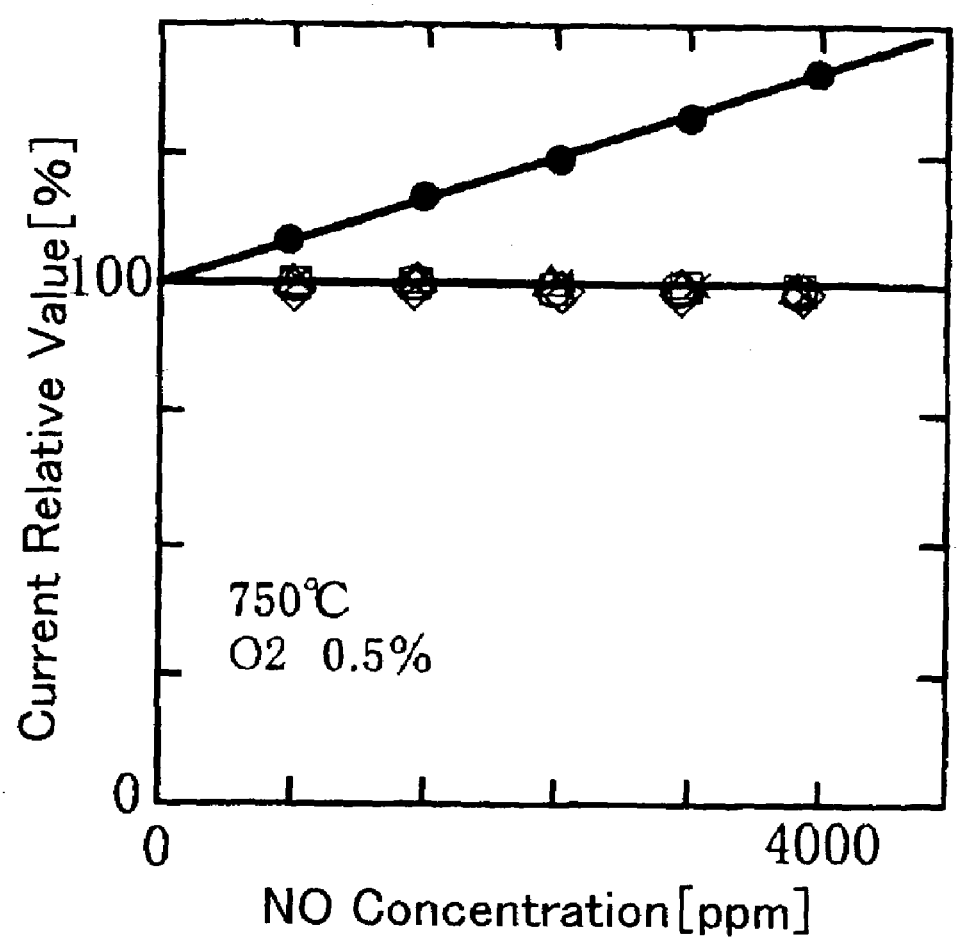
FIG. 18 is a graph showing a relationship between limiting current and the NO concentration of each of sample elements [1], [13], [20], [22], [29], and [30] when the nitrogen oxide gas (NO) was added to an oxygen atmosphere.

The flammable gas-oxygen combustion reactivity on a surface of each electrode were tested. The nitrogen gas reduction reactivity on a surface of each electrode were also tested. Herein, the current—voltage characteristic (IV characteristic) of each sample element, when 0 to 500 ppm of $C_3H_8$ as the flammable gas was added to an approximately 0.5% oxygen atmosphere at about 750° C., was measured. A change in limiting current obtained at the time was measured. FIG. 17 shows the relationships between the limiting currents (values relative to the currents) and the $C_3H_8$ concentrations. In addition, the current—voltage characteristic (IV characteristic) of each sample element, when 0 to 4000 ppm of NO as the nitrogen oxide gas was added to an approximately 0.5% oxygen atmosphere at about 750° C., was measured. A change in limiting current obtained at the time was evaluated. FIG. 18 shows the relationships between the limiting currents (values relative to the currents) and the NO concentrations.

The same tests were conducted for six sample elements [1], [13], [20], [22], [29], [30]. Sample element [1] was formed from $Ce_{0.8}Sm_{0.2}O_{2-\alpha}$. Sample element [13] was formed from 50% by mass of $Pr_{0.6}Sr_{0.4}MnO_{3-\alpha}$ and 50% by mass of $Ce_{0.8}Sm_{0.2}O_{2-\alpha}$. Sample element [20] was formed from a layered body that was obtained by bonding together a layer of $Ce_{0.8}Sm_{0.2}O_{2-\alpha}$ and a layer of $Pr_{0.6}Sr_{0.4}MnO_{3-60}$. Sample element [22] was formed from a layered body that was obtained by bonding together a layer of $Ce_{0.8}Sm_{0.2}O_{2-\alpha}$ and a layer of a mixture of 50% by mass of $Pr_{0.6}Sr_{0.4}MnO_{3-\alpha}$ and 50% by mass of $Ce_{0.8}Sm_{0.2}O_{2-\alpha}$. Sample element [29] was formed from 88% by mass of Pt, 2% by mass of Au, and 10% by mass of YSZ. Sample element [30] was formed from 90% by mass of Pt and 10% by mass of YSZ.

As shown in FIG. 17, in sample elements [1], [13], [20], [22], all of which include the electrodes containing $Ce_{0.8}Sm_{0.2}O_{2-\alpha}$, the limiting current changes were small even though $C_3H_8$ was added to the ambient atmosphere.

Similarly, as shown in FIG. 18, in sample elements [1], [13], [20], [22], all of which include the electrodes containing $Ce_{0.8}Sm_{0.2}O_{2-\alpha}$, the limiting current changes were small even though NO was added to the ambient atmosphere. As is understood from the results, the electrodes that contain $Ce_{0.8}Sm_{0.2}O_{2-\alpha}$ have low activity to $C_3H_8$ and NO. On the other hand, sample element [29] that includes the Pt—Au electrode and sample element [30] that includes the Pt electrode, the limiting currents decreased when $C_3H_8$ was added. As is understood from the results, the Pt—Au electrode and the Pt electrode both have high activity to $C_3H_8$ and hence high combustion reactivity between $C_3H_8$ and $O_2$. In addition, as shown in FIG. 18, in sample element [29] that includes Pt—Au electrode, the limiting current change was small when NO was added. It can been seen from the result that sample element [29] has low reactivity to NO. On the other hand, sample element [30] that has the Pt electrode exhibited the limiting current increase. It can been seen from the result that the sample element [30] has high activity to NO and hence high reduction reactivity to NO.

Accordingly, in each of the gas sensors of the sixth and the seventh embodiments, utilizing the oxide-containing electrode, as first inside electrode 144a of the first oxygen pump 142, makes it possible to obtain the oxygen pump that is capable of remarkably reducing the resistance of the element. And the oxygen pumps that is capable of selectively expelling or introducing the oxygen gas with little effect upon the flammable gas and the nitrogen oxide gas can be made even if the ambient atmosphere contains the oxygen gas, the flammable gas, the nitrogen oxide gas.

Formation and Evaluation of the Gas Sensor of the Fourth Embodiment

The foregoing gas sensor of the fourth embodiment, which is shown in FIG. 3, was formed. Specifically, diffusion control body 30 (insulation layer) having gas introducing hole 51 made through it; a ceramic sheet layer 34 (oxide ion conductive solid electrolyte) comprising zirconia stabilized by 6 mol % of yttria; and insulation layer 36 incorporating heater 38 were disposed in the form of a layered body with insulation layers 32 between the layers. Then, the layered body was baked at approximately 1500° C.

In addition, oxygen pumps 40, 46 were formed by using ceramic sheet 34. As one electrode (inactive electrode) of first oxygen pump 40, mixture electrode 42 of electrode number [13] in Table 3 was formed on one side of ceramic sheet 34. Similarly, as one electrode (active electrode) of second oxygen pump 46, Pt electrode 48 of electrode number [30] was formed on one side of ceramic sheet 34. Also, as the other electrode of first oxygen pump 40, Pt electrode 44 was formed on the other side of ceramic sheet 34. Similarly, as the other electrode of second oxygen pump 46, Pt electrode 50 was formed on the other side of ceramic sheet 34.

Figure 19:
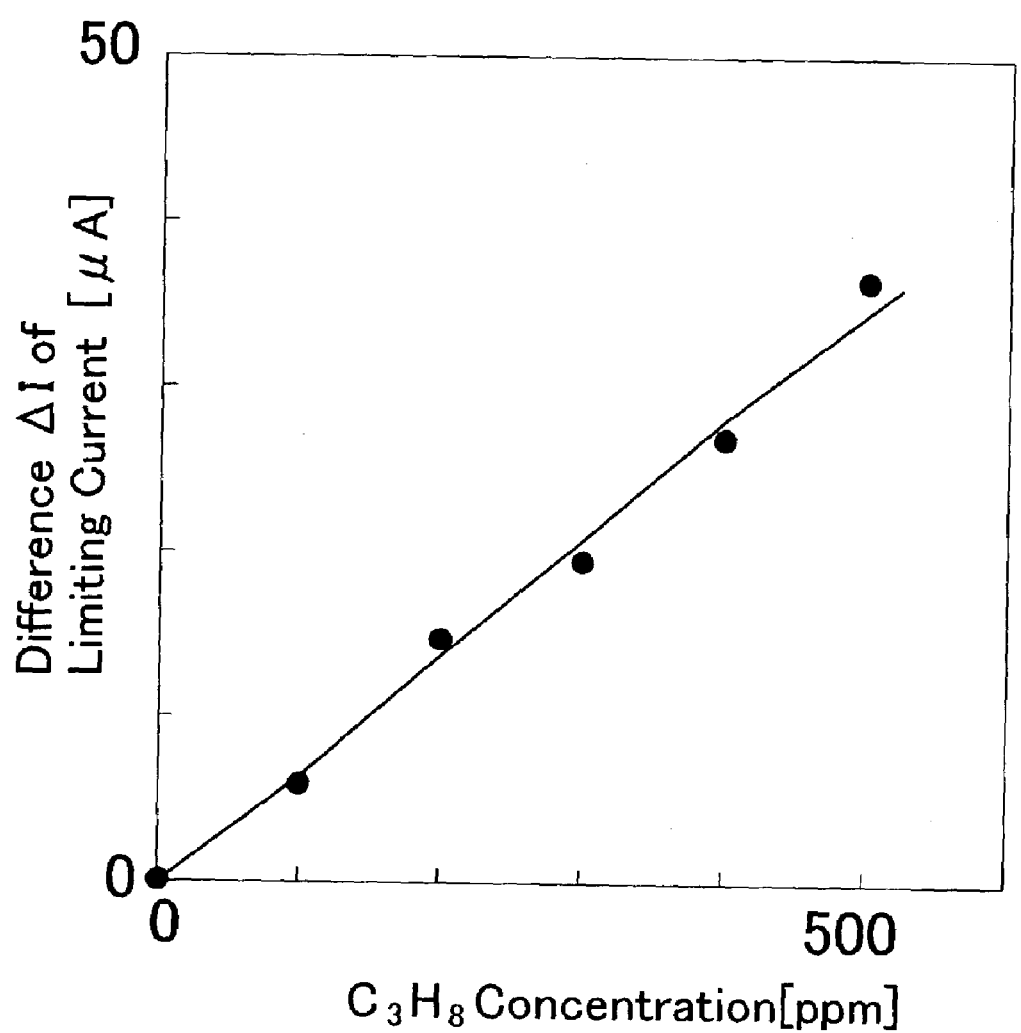
FIG. 19 is a graph showing a relationship between $C_3H_8$ concentration and the difference of limiting current between two oxygen pumps of the gas sensor according to the fourth representative embodiment.

The flammable gas concentration was measured by the limiting current difference between oxygen pumps 40, 46 in the following manner. First, the gas sensor that was formed in the above described manner was heated to 750° C. by heater 38 and then left in 10% $O_2$—$N_2$ atmosphere. Power sources 56a, 56b applied a voltage of 0.4V to oxygen pumps 40, 46, respectively. The currents that flowed when 0 to 500 ppm of $C_3H_8$ was added to the 10% $O_2$—$N_2$ atmosphere were measured by ammeter 58a, 58b In first oxygen pump 40 that includes foregoing mixture electrode 42 (inactive electrode), the limiting current hardly changed when $C_3H_8$ was added. Conversely, in second oxygen pump 46 that includes the Pt electrode 48 (active electrode), $C_3H_8$ and oxygen reacted on a surface of Pt electrode 48 and, therefore, the limiting current decreased as a quantity of $C_3H_8$ increased. The limiting current difference (sensor current difference) between oxygen pumps 40, 46 was plotted against the $C_3H_8$ concentration. FIG. 19 is a graph that shows the relationship between the limiting current difference and the $C_3H_8$ concentration. As shown in FIG. 19, the limiting current difference increases almost linearly relative to a quantity of $C_3H_8$ Accordingly, it is clear from the results that the flammable gas concentration can be accurately measured by the limiting current difference between first oxygen pump 40 having inactive electrode 42 and second oxygen pump 46 having active electrode 48.

Formation and Evaluation of the Gas Sensor of the Fifth Embodiment

The foregoing gas sensor of the fifth embodiment, which is shown in FIG. 4, was formed in combination with the oxygen pump and the electromotive force generation element. Ceramic sheets comprising zirconia stabilized by 6 mol % of yttria were utilized as oxide-ion conductive solid electrolyte 60. A layered body was formed in the following manner. Lower side insulation sheet 62 was disposed on insulation layer 64 incorporating heater 66. Ceramic sheet 60b having electrodes 76, 78, 80 formed thereon was disposed on lower side insulation sheet 62. Upper side insulation sheet 62 was disposed on ceramic sheet 60b. Ceramic sheet 60a having electrodes 70, 72 formed thereon was disposed on upper side insulation sheet 62. In this case, the layered body was formed so as to define gas detection chamber 84 between ceramic sheets 60a, 60b and reference gas introducing chamber 86 between sheet ceramic sheet 60b and insulation sheet 64. Thereafter, the layered body was baked at approximately 1500° C. Thus, the gas sensor of the fifth embodiment was obtained.

Mixture electrode 70 of electrode number [13] in Table 3 was screen printed on the gas detection chamber 84 side of ceramic sheet 60a in the similar manner to the foregoing sample elements. Pt electrode 72 having electrode number [30] was formed on the other side of ceramic sheet 60a, which is the side opposite to the gas detection chamber 84 side. Also, Pt electrode (active electrode) 76 and mixture electrode (inactive electrode) 78 of electrode number [13] were screen printed in the similar manner to the foregoing sample elements. As a reference electrode, Pt electrode 80 was formed on the opposite side of ceramic sheet 60b, which is the side opposite to the gas detection chamber 84.

Figure 20:
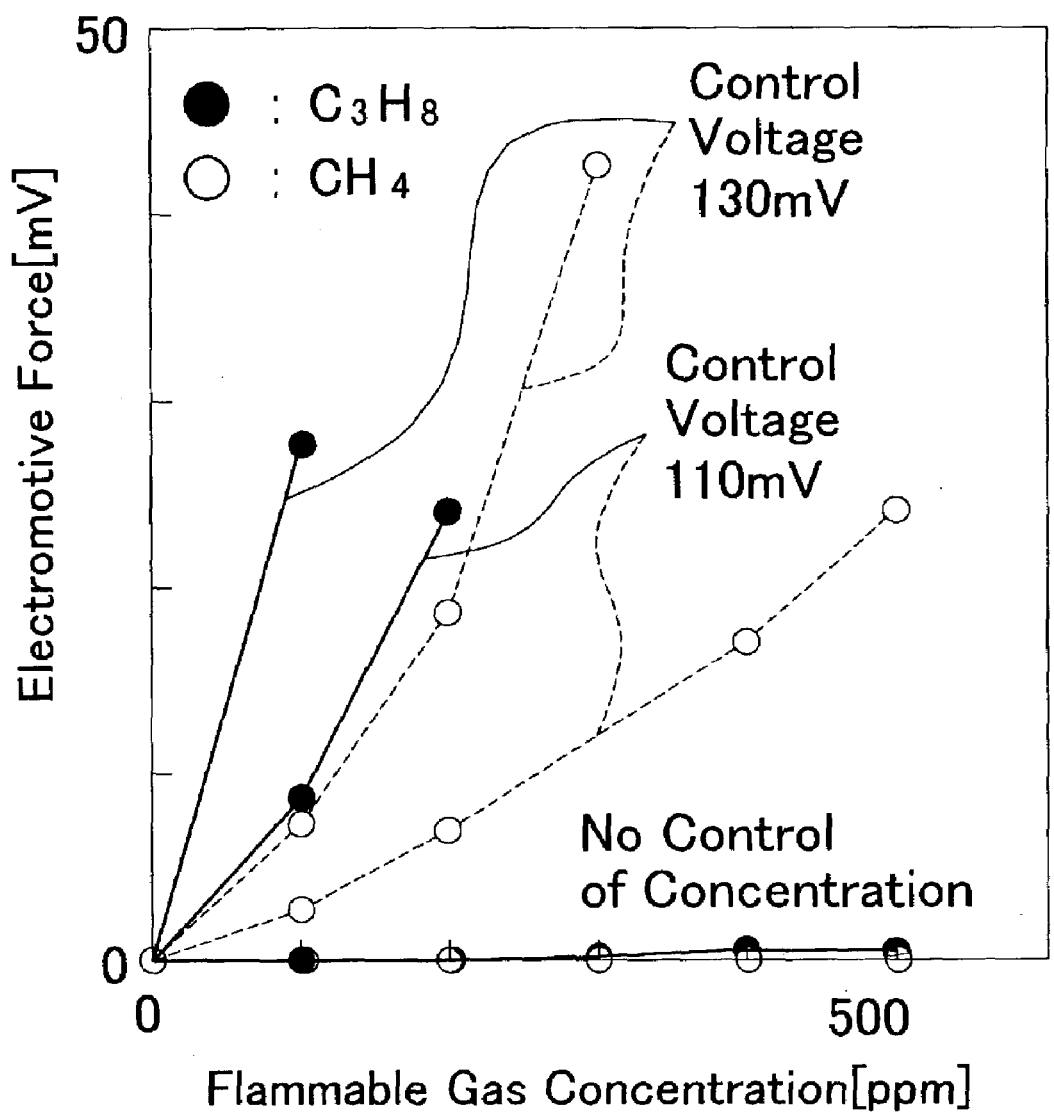
FIG. 20 is a graph showing a relationship between the concentration of each of the flammable gas and the electromotive force (i.e., electromotive force generated between an active electrode and an inactive electrode) when the oxygen concentration was controlled based upon the electromotive force generated between the inactive electrode and a reference electrode of an electromotive force generation element of the gas sensor according to the fifth representative embodiment.

The aforesaid gas sensor was heated to 750° C. and left in a 10% $O_2$—$N_2$ atmosphere. At the time, the oxygen concentration in the ambient atmosphere in gas detection chamber 84 was controlled based upon an electromotive force generated between inactive electrode 78 and reference electrode 80. In this case, a control voltage of 110 mV or 130 mV, which was calculated based upon the Nernst electromotive force, was used. If 110 mV was used, the oxygen concentration in gas detection chamber 84 was adjusted to approximately 0.15%. If 130 mV was used, the oxygen concentration in chamber 84 was adjusted to approximately 0.055%. Next, 0 to 500 ppm $CH_4$ (measurement gas) and 0 to 500 ppm $C_3H_8$ (measurement gas) were introduced into the ambient atmosphere in gas detection chamber 84. The electromotive force generated between active electrode 76 and inactive electrode 78 was measured. FIG. 20 is a graph that shows the relationships between the flammable gas concentrations and the electromotive forces (electromotive forces between active electrode 76 and inactive electrode 78) when the oxygen concentration was controlled based upon the electromotive force between inactive electrode 78 and reference electrode 80.

As shown in FIG. 20, the electromotive force between active electrode 76 and inactive electrode 78 varied according to the $CH_4$ concentration and the $C_3H_8$ concentration. Therefore, the concentrations of theses gases could be selectively measured by the electromotive force. In addition, as the control voltage was increased (i.e., as the oxygen concentration was decreased), the electromotive force was increased, which improves the capability of detecting a minute quantity of each of gases, $CH_4$ and $C_3H_8$.

Figure 21:
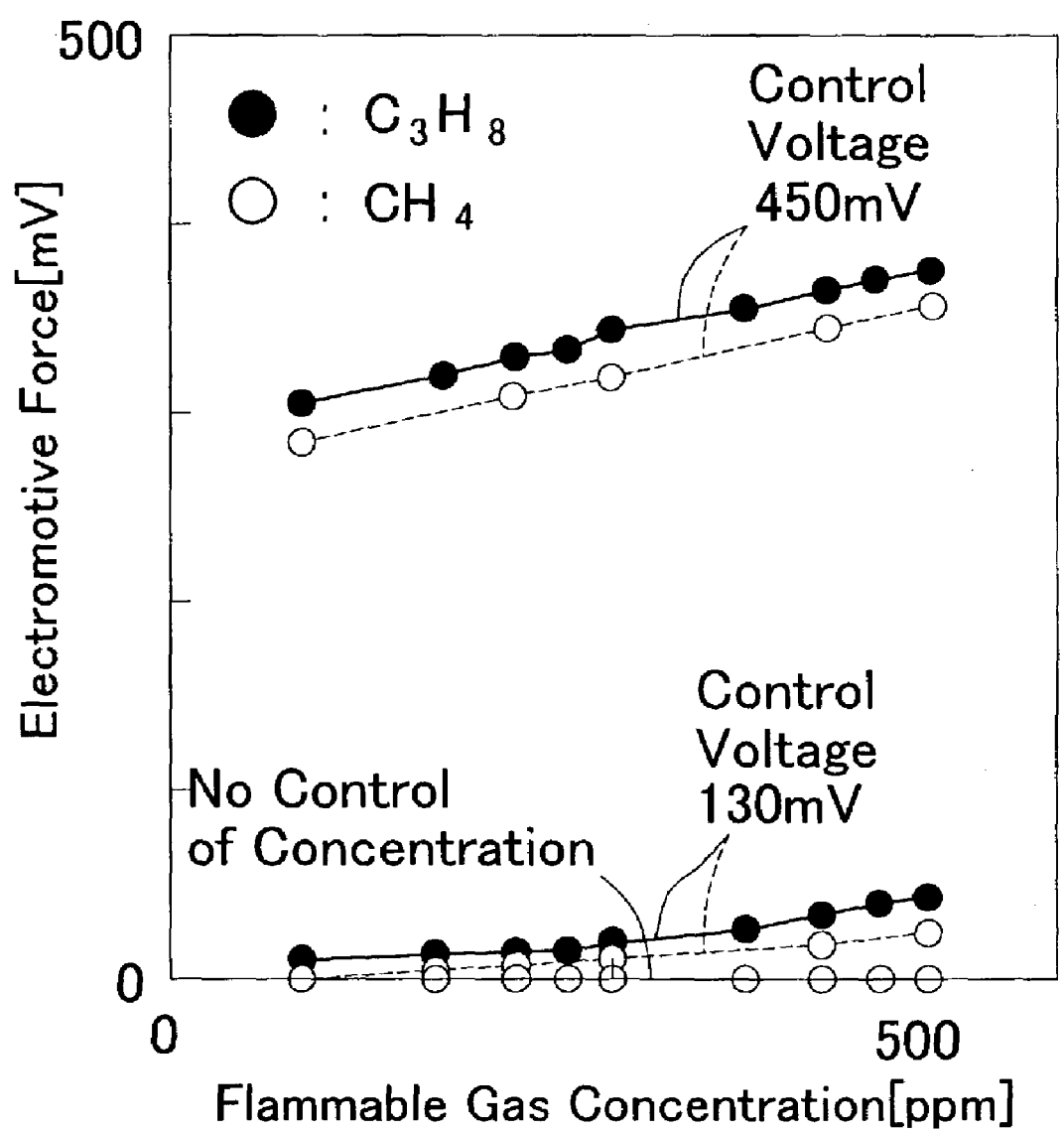
FIG. 21 is a graph showing a relationship between the concentration of each of flammable gas, which were the same as the gases in FIG. 20, and the electromotive force (i.e., electromotive force generated between the active electrode and the inactive electrode) when the oxygen concentration was controlled based upon the electromotive force generated between the active electrode and the reference electrode of the electromotive force generation element of the gas sensor according the fifth representative embodiment.

However, when the $CH_4$ concentration and the $C_3H_8$ concentration exceed certain values, the electromotive force increased. This is because the reactions of the oxygen in gas detection chamber 84 with $CH_4$ and $C_3H_8$ exceeded respective equivalence points, and consequently the oxygen concentration on the interface of active electrode 76 suddenly decreased. Therefore, this control allows the satisfactory gas concentration measurement only by the time the reaction of the oxygen in gas detection chamber 84 with the measurement gas reaches the equivalence point. In order to measure the flammable gas concentration over a wide range, the oxygen concentration needs to be adjusted to relatively high values On the other hand, FIG. 21 shows the relationships between the flammable gas concentrations and the electromotive forces (electromotive forces between active electrode 76 and inactive electrode 78) when the oxygen concentration was controlled based upon the electromotive force between active electrode 76 and reference electrode 80. Controlling the oxygen concentration by using active electrode 76 substantially means controlling the oxygen concentration near the interface between active electrode 76 and solid electrolyte 60b after the oxygen and flammable gas burned at the active electrode 76.

In this control, a control voltage of 130 mV or 450 mV was used, and the oxygen concentration on the interface between active electrode 76 and solid electrolyte 60b was adjusted to approximately 0.055% or $3 \times 10^{-8}$%. Because the electromotive force between active electrode 76 and inactive electrode 78 varies according to the $CH_4$ concentration and the $C_3H_8$ concentration, the concentrations of these gases could be selectively measured by the electromotive force. Unlike the oxygen concentration control based upon the electromotive force between inactive electrode 78 and reference electrode 80, the electromotive force between active electrode 76 and inactive electrode 78 did not change suddenly, so that the concentrations could be measured over a wide range from a low value to a high value. That is because the oxygen concentration after the combustion of the oxygen and the flammable gas ($CH_4$, $C_3H_8$) was controlled by active electrode 76 that has high catalytic activity, gas detection chamber 84 became constantly full of oxygen and, as a result, the ratio of oxygen and flammable gas near the interface of active electrode 76 did not exceed the equivalence point any longer. Accordingly, by utilizing such control, the flammable gas (hydrocarbon gas) concentration could be selectively and highly accurately measured over a wide range.

Formation and Evaluation of Gas Concentration Measurement Device of the Sixth Embodiment The foregoing gas sensor of the sixth embodiment, which is shown in FIG. 5, was fabricated in the following manner. Ceramic sheets comprising zirconia stabilized by 6 mol % of yttria were utilized respectively as upper solid electrolyte 130 and lower solid electrolyte 130, both of which are oxide-ion conductive. A layered body was formed in the following manner. Insulation sheet 128 was disposed on insulation layer 126 incorporating beater 122. Ceramic sheet 130 having electrodes 144a, 144b formed thereon was disposed on insulation sheet 128. Insulation sheet 132, 184 and diffusion control layers 176, 180 was disposed on ceramic sheet 130. Ceramic sheet 130 having electrodes 154a, 154b, 164a, 164b formed thereon was disposed on insulation sheet 132, 184 and diffusion control layers 176, 180. Diffusion control layer 136 and insulation sheet 174 was disposed on ceramic sheet 130. In this case, the layered body was formed so as to define atmospheric air communication passage 124 between insulation sheets 126 and ceramic sheet 130. The layered body was formed so as to define chamber parts 140a, 140b, 140c between ceramic sheet 130. The layered body was formed so as to define atmospheric air communication passage 172 between ceramic sheet 130 and insulation sheets 174. Thereafter, the layered body was baked at approximately 1500° C. As a result, the gas sensor of FIG. 5 was obtained.

On the first chamber 140a side (upper side) of ceramic sheet 130, mixture electrode 144a of electrode number [13] in Table 3 was formed as first inside electrode by screen printing in the similar manner to the aforesaid sample elements. On the side opposite to the first chamber 140a side (lower side) of ceramic sheet 130, Pt electrode 144b of electrode number [30] was formed as first outside electrode. Also, on the second chamber 140b side (lower side) of ceramic sheet 130, Pt—Au electrode 154a of electrode number [29] was formed as second inside electrode. On the side opposite to the second chamber 140b side (upper side) of ceramic sheet 130, Pt electrode 154b was formed as second outside electrode. Further, on the third chamber 140c side (lower side) of ceramic sheet 130, Pt electrode 164a was formed as the third inside electrode. On the side opposite to the third chamber 140c side (upper side) of ceramic sheet 130, Pt electrode 164b was formed as third outside electrode.

Each of oxygen pumps 142, 152, 162 of the thus formed gas sensor was driven by the application of a voltage of 0.3 V to each oxygen pump. Then, in the ambient atmosphere containing $O_2$, $C_3H_8$, and NO, the concentration of $O_2$, $C_3H_8$, or NO, for use as a parameter gas, was changed in order to evaluate the limiting current change of each oxygen pump 142, 152, 162. The concentration of $O_2$, when not in use as the parameter gas, was 0.5%. The concentrations of $C_3H_8$ and NO, when not in use as the parameter gases, were 300 ppm and 2000 ppm, respectively.

Figure 22:
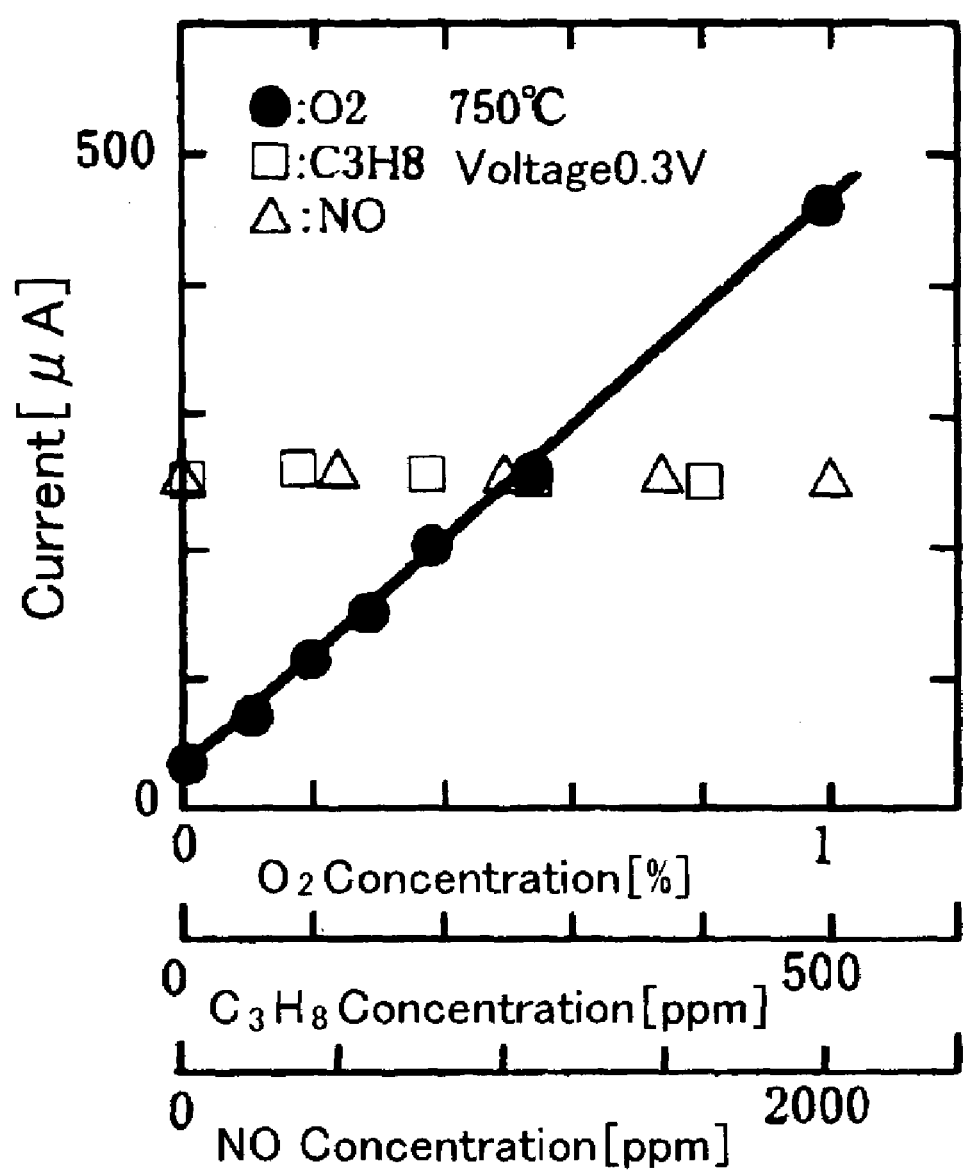
FIG. 22 is a graph showing a relationship between the concentration of each of gases, $O_2$, $C_3H_8$, and NO, and the limiting current in a first oxygen pump of the gas sensor according to the sixth representative embodiment.
Figure 23:
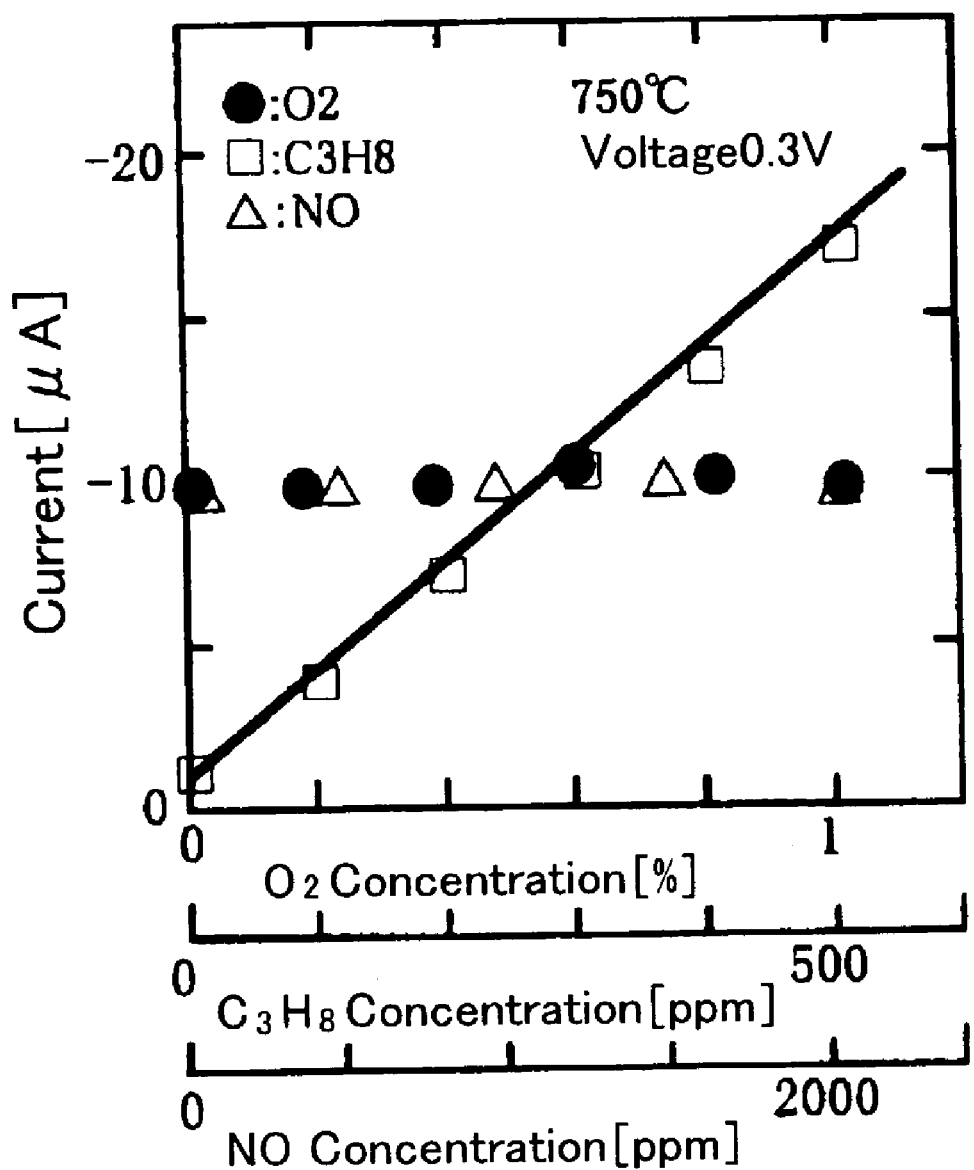
FIG. 23 is a graph showing a relationship between the concentration of each of gases, $O_2$, $C_3H_8$, and NO, and the limiting current in a second oxygen pump of the gas sensor according to the sixth representative embodiment.
Figure 24:
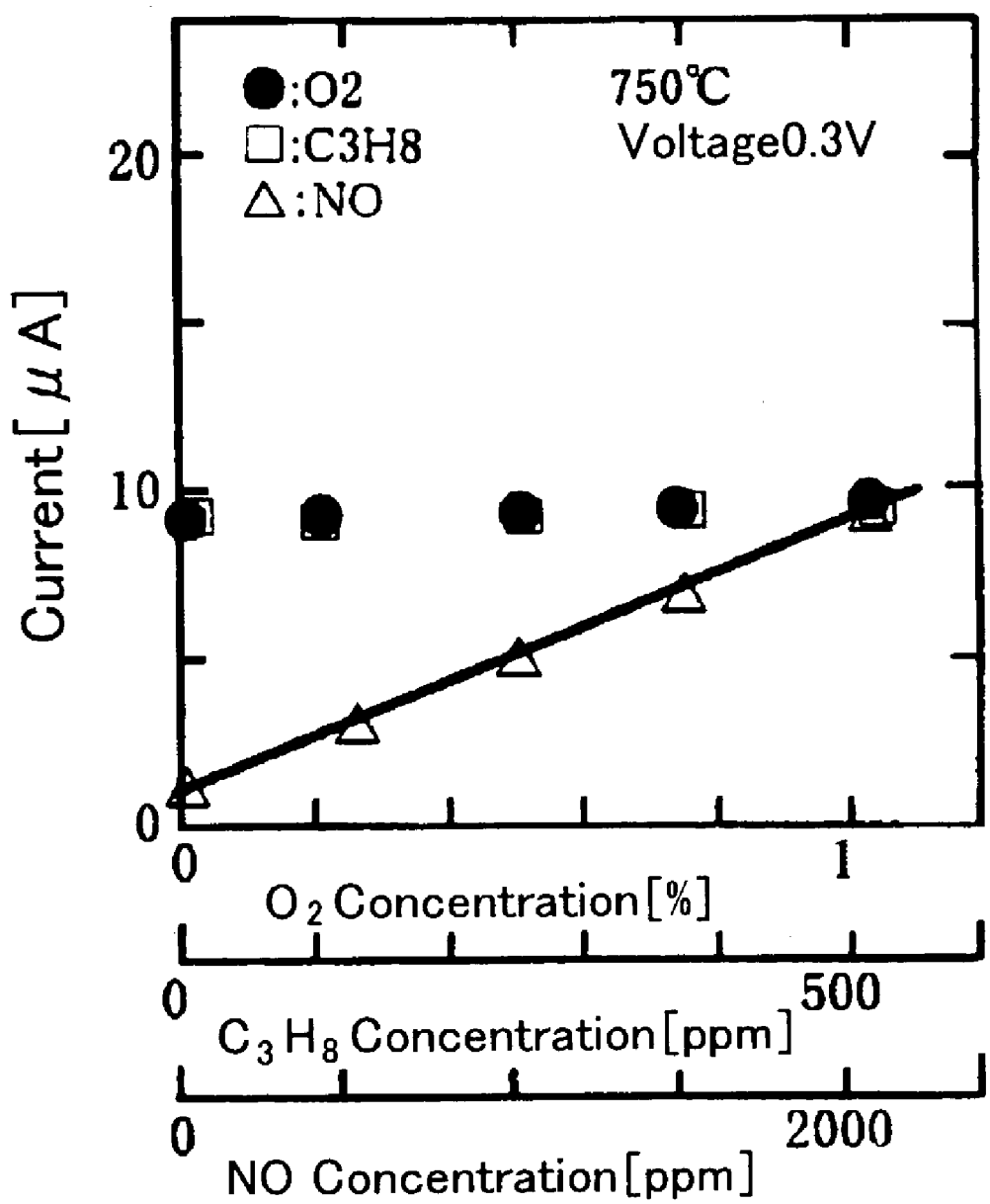
FIG. 24 is a graph showing a relationship between the concentration of each of gases, $O_2$, $C_3H_8$, and NO, and the limiting current in a third oxygen pump of the gas sensor according to the sixth representative embodiment.
Figure 25:
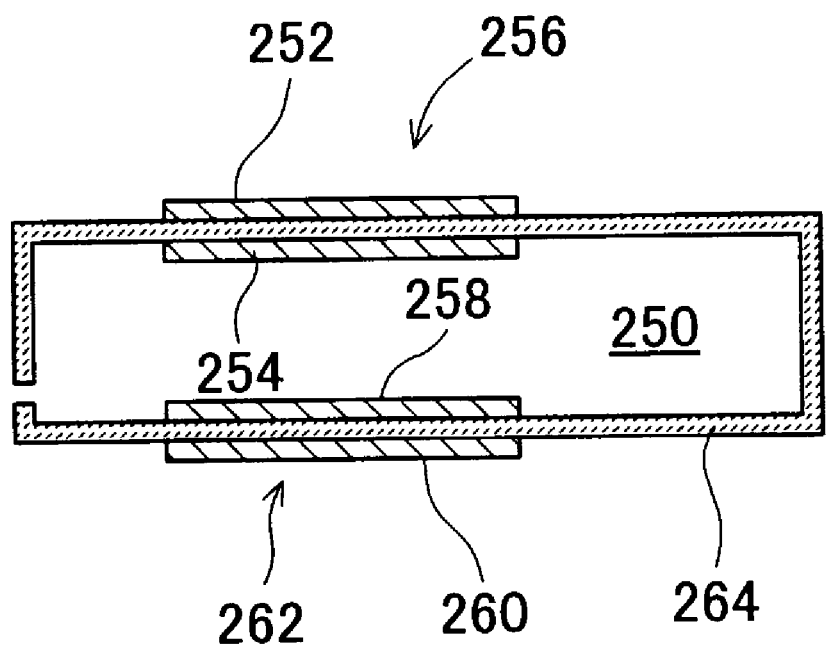
FIG. 25 is a schematic cross-sectional view of a gas sensor according to the related art.

FIG. 22 shows the relationship between the limiting current of first oxygen pump 142 and the $O_2$, $C_3H_8$, and NO gas concentrations. FIG. 23 shows the relationship between the limiting current of second oxygen pump 152 and the $O_2$, $C_3H_8$, and NO gas concentrations. FIG. 24 shows the relationship between the limiting current of third oxygen pump 162 and the $O_2$, $C_3H_8$, and NO gas concentrations. As shown in FIG. 22, in first oxygen pump 142, even when the $C_3H_8$ concentration and the NO concentration increased, the limiting current flowing through first oxygen pump 142 hardly changed. On the other hand, when the $O_2$ concentration increased, the limiting current flowing through first oxygen pump 142 increased substantially in proportion to the $O_2$ concentration. As shown in FIG. 23, in second oxygen pump 152, even when the $O_2$ concentration and the NO concentration increased, the limiting current flowing through second oxygen pump 152 hardly changed. Contrarily, when the $C_3H_8$ concentration increased, the limiting current flowing through second oxygen pump 152 increased substantially in proportion to the $C_3H_8$ concentration. As shown in FIG. 24, in third oxygen pump 162, even when the $O_2$ concentration and $C_3H_8$ increased, the limiting current flowing through third oxygen pump 162 hardly changed. Conversely, when the NO concentration increased, the limiting current flowing through third oxygen pump 162 increased substantially in proportion to the NO concentration.

The results showed that first oxygen pump 142 has high $O_2$ selectivity (quantitativity), second oxygen pump 152 has high $C_3H_8$ selectivity (quantitativity), and third oxygen pump 162 has high NO selectivity (quantitativity). Accordingly, by utilizing the gas sensor, the $O_2$ gas, the $C_3H_8$ gas, and the NO gas can be selectively and highly accurately measured (quantified) when the measurement gas contains these gases.

The result were obtained by virtue of the utilization of the aforesaid mixture electrode (one of the examples of the aforementioned oxide-containing electrode), as first inside electrode 144a of first oxygen pump 142, which has very high activity to $O_2$ and low activity to $C_3H_8$ and NO. Also, the result were obtained by virtue of the utilization of the Pt—Au electrode (one of the examples of the electrode that contains Au), as second inside electrode 154a of second oxygen pump 152, which has high activity to $C_3H_8$ and low activity to NO. Further, the result were obtained by virtue of the utilization of Pt electrode (one of the examples of the electrode that contains at least Pt, Pd, Rh, Ag, or Ni), as third inside electrode 164a of third oxygen pump 162, which has high activity to NO.

That is to say, the aforesaid mixture electrode that serves as first inside electrode 144a of first oxygen pump 142 has very high activity to $O_2$ and low activity to $C_3H_8$ and NO. Therefore, $O_2$ can be selectively and highly accurately measured (quantified). The Pt—Au electrode that is second inside electrode 154a of second oxygen pump 152 has high activity to both $C_3H_8$ and $O_2$. However, oxygen has been selectively and sufficiently reduced by first oxygen pump 142 that utilizes the aforesaid mixture electrode as first inside electrode 144a. In addition, in first oxygen pump 142, the reaction of $C_3H_8$ has hardly occurred. Accordingly, second oxygen pump 152 selectively and highly accurately measures (quantifies) $C_3H_8$. The Pt electrode that is third inside electrode 164a of third oxygen pump 162 is active to not only NO but also $O_2$ and $C_3H_8$. However, as described above, in first oxygen pump 142, oxygen has been selectively and sufficiently reduced and the reaction of NO has hardly occurred. Also, in second oxygen pump 152 that utilizes the Pt—Au electrode as second inside electrode 154a, the flammable gas has been sufficiently burned and the reaction of NO has hardly occurred. As a result, third oxygen pump 162 selectively and highly accurately measures (quantifies) NO.

In another aspect of the present teachings, a gas sensor may include a first oxygen pump and a second oxygen pump. The first oxygen pump may include the first electrode. The first electrode is preferably the aforesaid oxide-containing electrode. The second oxygen pump may include a second electrode. The second electrode is preferably active to promote oxidation of flammable gas or reduction of nitrogen oxide gas.

In yet another aspect of the present teachings, a gas sensor may include a first oxygen pump and a first measurement element. The first oxygen pump may include the first electrode. The first electrode is preferably the aforesaid oxide-containing electrode. The first measurement element may measure a quantity of flammable gas or nitrogen oxide gas.

Preferably, the first measurement element includes an electrochemical element. Preferably, the electrochemical element includes an electromotive force generation element. Preferably, the electromotive force generation element includes the aforesaid oxide-containing electrode.

Preferably, the electrochemical element includes a second oxygen pump. Preferably, the second oxygen pump includes a second electrode including Au or an alloy containing Au. The gas sensor further may include a second measurement element for measuring a quantity of nitrogen oxide gas. More preferably, the second measurement element includes a third oxygen pump.

The invention claimed is:

1. An electrochemical element comprising:
an oxide-ion conductive solid electrolyte; and
an electrode comprising at least one component selected from a group consisting of (III) and (IV);
(I) a perovskite oxide expressed by $(A_{1-x}B_x)(C_{1-y}D_y)O_{3-z}$,
(II) an oxide expressed by $(Ce_{1-x}P_x)O_{2-z}$,
(III) a mixture of said (I) and said (II), the proportion of said (II) in the mixture being 1 to 95% by weight; and
(IV) a layered body formed by at least two layers, each layer including at least one component selected from a group consisting of said (I), said (II) and the mixture of said (I) and (II); wherein in (I) through (IV);
symbol A represents La, Pr, Ce, Ca, Sr, or Ba;
symbol B represents Sr, Ce or Ca;
symbol C represents Cr, Mn, Fe, Co, Ti, Zr, or Ga;
symbol D represents Cr, Ni, Mg, Zr, Ce, Fe, Al, or Co, and
symbol P represents La, Pr, Nd, Sm, Eu, Gd, Tb, Dy, Tm, Yb, Ca, Y, Mg, Sr, Ba, Zr, Mn, Fe, or Cr,
wherein X satisfies the condition of $0 \leq X \leq 0.5$ and Y satisfies the condition of $0 \leq Y \leq 0.5$,
wherein the oxide-ion conductive solid electrolyte and the electrode are in contact with each other or are next to each other with another member between them.

2. A gas sensor, comprising:
an oxide-ion conductive solid electrolyte for forming at least a part of a wall surrounding a gas detection chamber;
a first electrode disposed within the gas detection chamber such that the oxide-ion conductive solid electrolyte and the first electrode are in contact with each other or are next to each other with another member between them; and
a second electrode disposed within the gas detection chamber such that the oxide-ion conductive solid electrolyte and the second electrode are in contact with each other or are next to each other with another member between them, wherein the second electrode is active to promote oxidation of flammable gas or reduction of nitrogen oxide gas,
wherein the first electrode comprises at least one component selected from a group consisting of (III) and (IV);
(I) a perovskite oxide expressed by $(A_{1-x}B_x)(C_{1-y}D_y)O_{3-z}$,
(II) an oxide expressed by $(Ce_{1-x}P_x)O_{2-z}$,
(III) a mixture of said (I) and said (II), the proportion of said (II) in the mixture being 1 to 95% by weight; and
(IV) a layered body formed by at least two layers, each layer including at least one component selected from a group consisting of said (I), said (II) and the mixture of said (I) and (II); wherein in (I) through (IV);

symbol A represents La, Pr, Ce, Ca, Sr, or Ba;
symbol B represents Sr, Ce or Ca;
symbol C represents Cr, Mn, Fe, Co, Ti, Zr, or Ga;
symbol D represents Cr, Ni, Mg, Zr, Ce, Fe, Al, or Co, and
symbol P represents La, Pr, Nd, Sm, Eu, Gd, Tb, Dy, Tm, Yb, Ca, Y, Mg, Sr, Ba, Zr, Mn, Fe, or Cr,
wherein X satisfies the condition of $0 \leq X \leq 0.5$ and Y satisfies the condition of $0 \leq Y \leq 0.5$.

3. A gas sensor comprising:
an oxide-ion conductive solid electrolyte for forming at least a part of a wall surrounding a gas detection chamber;
a first inner electrode disposed within the gas detection chamber such that the oxide-ion conductive solid electrolyte and the first inner electrode are in contact with each other or are next to each other with another member between them;
a first outer electrode disposed at an outer surface of the oxide-ion conductive solid electrolyte such that the oxide-ion conductive solid electrolyte and the first outer electrode are in contact with each other or next to each other with another member between them; and
a first measurement element measuring a quantity of flammable gas or nitrogen oxide gas in the gas detection chamber;
wherein the first inner electrode and the first outer electrode are to be electrically coupled via a ammeter and a voltage source; and
wherein the first inner electrode comprises at least one component selected from a group consisting of (III) and (IV);
(I) a perovskite oxide expressed by $(A_{1-x}B_x)(C_{1-y}D_y)O_{3-z}$,
(II) an oxide expressed by $(Ce_{1-x}P_x)O_{2-z}$,
(III) a mixture of said (I) and said (II), the proportion of said (II) in the mixture being 1 to 95% by weight; and
(IV) a layered body formed by at least two layers, each layer including at least one component selected from a group consisting of said (I), said (II) and the mixture of said (I) and (II); wherein in (I) through (IV);
symbol A represents La, Pr, Ce, Ca, Sr, or Ba;
symbol B represents Sr, Ce or Ca;
symbol C represents Cr, Mn, Fe, Co, Ti, Zr, or Ga;
symbol D represents Cr, Ni, Mg, Zr, Ce, Fe, Al, or Co, and
symbol P represents La, Pr, Nd, Sm, Eu, Gd, Th, Dy, Tm, Yb, Ca, Y, Mg, Sr, Ba, Zr, Mn, Fe, or Cr,
wherein X satisfies the condition of $0 \leq X \leq 0.5$ and Y satisfies the condition of $0 \leq Y \leq 0.5$.

4. A sensor as in claim 3, wherein the first measurement element comprises
a second inner electrode disposed within the gas detection chamber such that the oxide-ion conductive solid electrolyte and the second inner electrode are in contact with each other or are next to each other with another member between them.

5. A sensor as in claim 4, wherein the second inner electrode comprises Au or an alloy containing Au; and the sensor further comprising a second measurement element for measuring a quantity of nitrogen oxide gas in the gas detection chamber.

6. A sensor as in claim 5, wherein the second measurement element comprises
a third inner electrode disposed within the gas detection chamber such that the oxide-ion conductive solid electrolyte and the third inner electrode are in contact with each other or are next to each other with another member between them;

a third outer electrode disposed at the outer surface of the oxide-ion conductive solid electrolyte such that the oxide-ion conductive solid electrolyte and the third outer electrode are in contact with each other or next to each other with another member between them;
wherein the third inner electrode and the third outer electrode are to be electrically coupled via a ammeter and a voltage source.

7. A sensor as in claim 6, wherein the third inner electrode comprises at least one component selected from a group consisting of Pt, Pd, Rh, Ag, and Ni.

8. A gas measurement method comprising:
introducing mixture gas into a gas detection chamber under a predetermined diffusion resistance; and
measuring a difference or a ratio between a limiting current flowing a first oxygen pump and a limiting current flowing a second oxygen pump, wherein
the first oxygen pump comprises a first electrode in the gas detection chamber and wherein the second oxygen pump comprises a second electrode being active to promote oxidation of flammable gas or reduction of nitrogen oxide gas in the gas detection chamber,
wherein the first electrode comprises at least one component selected from a group consisting of (III) and (IV);
(I) a perovskite oxide expressed by $(A_{1-x}B_x)(C_{1-y}D_y)O_{3-z}$,
(II) an oxide expressed by $(Ce_{1-x}P_x)O_{2-z}$,
(III) a mixture of said (I) and said (II), the proportion of said (II) in the mixture being 1 to 95% by weight; and
(IV) a layered body formed by at least two layers, each layer including at least one component selected from a group consisting of said (I), said (II) and the mixture of said (I) and (II); wherein in (I) through (IV);
symbol A represents La, Pr, Ce, Ca, Sr, or Ba;
symbol B represents Sr, Ce or Ca;
symbol C represents Cr, Mn, Fe, Co, Ti, Zr, or Ga;
symbol D represents Cr, Ni, Mg, Zr, Ce, Fe, Al, or Co, and
symbol P represents La, Pr, Nd, Sm, Eu, Gd, Th, Dy, Tm, Yb, Ca, Y, Mg, Sr, Ba, Zr, Mn, Fe, or Cr,
wherein X satisfies the condition of $0 \leq X \leq 0.5$ and Y satisfies the condition of $0 \leq Y \leq 0.5$.

9. A gas measurement method comprising:
introducing mixture gas into a gas detection chamber under a predetermined diffusion resistance;
expelling or introducing oxygen in the gas detection chamber by utilizing a controlling oxygen pump, wherein the controlling oxygen pump comprises the first inner electrode disposed within the gas detection chamber; and
measuring a quantity of flammable gas or nitrogen oxide gas in the gas detection chamber,
wherein the first electrode comprises at least one component selected from a group consisting of (III) and (IV);
(I) a perovskite oxide expressed by $(A_{1-x}B_x)(C_{1-y}D_y)O_{3-z}$,
(II) an oxide expressed by $(Ce_{1-x}P_x)O_{2-z}$,
(III) a mixture of said (I) and said (II), the proportion of said (II) in the mixture being 1 to 95% by weight; and
(IV) a layered body formed by at least two layers, each layer including at least one component selected from a group consisting of said (I), said (II) and the mixture of said (I) and (II); wherein in (I) through (IV);
symbol A represents La, Pr, Ce, Ca, Sr, or Ba;
symbol B represents Sr, Ce or Ca;
symbol C represents Cr, Mn, Fe, Co, Ti, Zr, or Ga;

symbol D represents Cr, Ni, Mg, Zr, Ce, Fe, Al, or Co, and
symbol P represents La, Pr, Nd, Sm, Eu, Gd, Th, Dy, Tm, Yb, Ca, Y, Mg, Sr, Ba, Zr, Mn, Fe, or Cr,
wherein X satisfies the condition of $0 \leq X \leq 0.5$ and Y satisfies the condition of $0 \leq Y \leq 0.5$.

10. A method as in claim 9, wherein a quantity of flammable gas or nitrogen oxide gas is measured by utilizing an electrochemical element,
wherein the electrochemical element comprises an inactive electrode disposed within the gas detection chamber, an active electrode disposed within the gas detection chamber, an reference electrode disposed outside of the gas detection chamber, and a voltmeter disposed between the inactive electrode and the active electrode,
wherein the voltmeter measures a electromotive force generated between the inactive electrode and the active electrode.

11. A method as in claim 10, wherein a quantity of flammable gas is measured by utilizing an electromotive force generation element; and
the method further comprising controlling oxygen partial pressure in the gas detection chamber to $10^{-7}$ to $10^{-2}$ atm based upon an electromotive force generated between the inactive electrode and the reference electrode of the electromotive force generation element.

12. A method as in claim 10, wherein a quantity of flammable gas is measured by utilizing an electromotive force generation element; and
the method further comprising controlling oxygen partial pressure to $10^{-12}$ to $10^{-3}$ atm based upon an electromotive force generated between the active electrode and the reference electrode of the electromotive force generation element, wherein the oxygen partial pressure is near the active electrode in the gas detection chamber after flammable gas was oxidized.

13. A method as in claim 9, wherein a quantity of flammable gas is measured by utilizing a second oxygen pump comprising a second inner electrode, wherein the second inner electrode comprises Au or an alloy containing Au, and wherein the second inner electrode is disposed within the gas detection chamber; and
the method further comprising measuring a quantity of the nitrogen oxide gas in the gas detection chamber.

14. A method as in claim 13, wherein a quantity of nitrogen oxide gas is measured by utilizing a third oxygen pump.

15. A gas sensor, comprising:
an oxide-ion conductive solid electrolyte for forming at least a part of a wall surrounding a gas detection chamber;
a first inner electrode disposed within the gas detection chamber such that the oxide-ion conductive solid electrolyte and the first inner electrode are in contact with each other or are next to each other with another member between them;
a first outer electrode disposed at an outer surface of the oxide-ion conductive solid electrolyte such that the oxide-ion conductive solid electrolyte and the first outer electrode are in contact with each other or next to each other with another member between them;
a pair of second inner electrodes disposed within the gas detection chamber such that the oxide-ion conductive solid electrolyte and the second inner electrode are in contact with each other or are next to each other with another member between them, wherein one of the second inner electrodes is active for promoting oxidation of flammable gas, and the other of the second inner electrodes is inactive for promoting oxidation of flammable gas; and
a second outer electrode disposed at an outer surface of the oxide-ion conductive solid electrolyte such that the oxide-ion conductive solid electrolyte and the second outer electrode are in contact with each other or next to each other with another member between them;
wherein the first inner electrode and the first outer electrode are to be electrically coupled via an ammeter and a voltage source,
wherein at least two of a first voltmeter, a second voltmeter and a third voltmeter are to be disposed in the first measurement element,
wherein the first voltmeter is to be disposed between the one of the second inner electrodes and the other of the second inner electrodes,
wherein the second voltmeter is to be disposed between the one of the second inner electrodes and the second outer electrode,
wherein the third voltmeter is to be disposed between the other of the second inner electrodes and the second outer electrode,
wherein the first inner electrode comprises at least one component selected from the group consisting of (I) to (IV);
(I) a perovskite oxide expressed by $(A_{1-x}B_x)(C_{1-y}D_y)O_{3-z}$,
(II) an oxide expressed by $(Ce_{1-x}P_x)O_{2-z}$,
(III) a mixture of said (I) and said (II), the proportion of said (II) in the mixture being 1 to 95% by weight; and
(IV) a layered body formed by at least two layers, each layer including at least one component selected from a group consisting of said (I), said (II) and the mixture of said (I) and (II); wherein in (I) through (IV);
symbol A represents La, Pr, Ce, Ca, Sr, or Ba;
symbol B represents Sr, Ce or Ca;
symbol C represents Cr, Mn, Fe, Co, Ti, or Zr;
symbol D represents Cr, Ni, Zr, Ce, Fe, Al, or Co, being different from symbol C, and
symbol P represents La, Pr, Nd, Sm, Eu, Gd, Tb, Dy, Tm, Yb, Ca, Y, Mg, Sr, Ba, Zr, Mn, Fe, or Cr,
wherein X satisfies the condition of $0 \leq X \leq 0.5$ and Y satisfies the condition of $0 \leq Y \leq 0.5$,
wherein the inactive electrode comprises at least one component selected from the group consisting of (III) and (IV);
(I) a perovskite oxide expressed by $(A_{1-x}B_x)(C_{1-y}D_y)O_{3-z}$,
(II) an oxide expressed by $(Ce_{1-x}P_x)O_{2-z}$,
(III) a mixture of said (I) and said (II), the proportion of said (II) in the mixture being 1 to 95% by weight; and
(IV) a layered body formed by at least two layers, each layer including at least one component selected from a group consisting of said (I), said (II) and the mixture of said (I) and (II); wherein in (I) through (IV);
symbol A represents La, Pr, Ce, Ca, Sr, or Ba;
symbol B represents Sr, Ce or Ca;
symbol C represents Cr, Mn, Fe, Co, Ti, Zr, or Ga;
symbol D represents Cr, Ni, Mg, Zr, Ce, Fe, Al, or Co, and
symbol P represents La, Pr, Nd, Sm, Eu, Gd, Tb, Dy, Tm, Yb, Ca, Y, Mg, Sr, Ba, Zr, Mn, Fe, or Cr,
wherein X satisfies the condition of $0 \leq X \leq 0.5$ and Y satisfies the condition of $0 \leq Y \leq 0.5$.

16. A gas sensor, comprising:

an oxide-ion conductive solid electrolyte for forming at least a part of a wall surrounding a gas detection chamber;

a first inner electrode disposed within the gas detection chamber such that the oxide-ion conductive solid electrolyte and the first inner electrode are in contact with each other or are next to each other with another member between them;

a first outer electrode disposed at an outer surface of the oxide-ion conductive solid electrolyte such that the oxide-ion conductive solid electrolyte and the first outer electrode are in contact with each other or next to each other with another member between them;

a pair of second inner electrodes disposed within the gas detection chamber such that the oxide-ion conductive solid electrolyte and the second inner electrodes are in contact with each other or are next to each other with another member between them, wherein one of the second inner electrodes is active for promoting oxidation of flammable gas, and the other of the second inner electrodes is inactive for promoting oxidation of flammable gas; and a second outer electrode disposed at an outer surface of the oxide-ion conductive solid electrolyte such that the oxide-ion conductive solid electrolyte and the second outer electrode are in contact with each other or next to each other with another member between them;

wherein the first inner electrode and the first outer electrode are to be electrically coupled via an ammeter and a voltage source, wherein at least two of a first voltmeter, a second voltmeter and a third voltmeter are to be disposed in the first measurement element, wherein the first voltmeter is to be disposed between the one of the second inner electrodes and the other of the second inner electrodes, wherein the second voltmeter is to be disposed between the one of the second inner electrodes and the second outer electrode, wherein the third voltmeter is to be disposed between the other of the second inner electrodes and the second outer electrode, wherein the first inner electrode comprises at least one component selected from the group consisting of (III) to (IV);

(I) a perovskite oxide expressed by $(A_{1-x}B_x)(C_{1-y}D_y)O_{3-z}$, (II) an oxide expressed by $(Ce_{1-x}P_x)O_{2-z}$, (III) a mixture of said (I) and said (II), the proportion of said (II) in the mixture being 1 to 95% by weight; and (IV) a layered body formed by at least two layers, each layer including at least one component selected from a group consisting of said (I), said (II) and the mixture of said (I) and (II); wherein in (I) through (IV);

symbol A represents La, Pr, Ce, Ca, Sr, or Ba;

symbol B represents Sr, Ce or Ca;

symbol C represents Cr, Mn, Fe, Co, Ti, or Zr;

symbol D represents Cr, Ni, Zr, Ce, Fe, Al, or Co, being different from symbol C, and symbol P represents La, Pr, Nd, Sm, Eu, Gd, Tb, Dy, Tm, Yb, Ca, Y, Mg, Sr, Ba, Zr, Mn, Fe, or Cr, wherein X satisfies the condition of $0 \leq X \leq 0.5$ and Y satisfies the condition of $0 \leq Y \leq 0.5$.

17. A sensor as in claim 16, wherein the inactive electrode comprises at least one component selected from a group consisting of (I) to (IV);

(I) a perovskite oxide expressed by $(A_{1-x}B_x)(C_{1-y}D_y)O_{3-z}$, (II) an oxide expressed by $(Ce_{1-x}P_x)O_{2-z}$, (III) a mixture of said (I) and said (II), the proportion of said (II) in the mixture being 1 to 95% by weight; and (IV) a layered body formed by at least two layers, each layer including at least one component selected from a group consisting of said (I) said (II) and the mixture of said (I) and (II); wherein in (I) through (IV);

symbol A represents La, Pr, Ce, Ca, Sr, or Ba;

symbol B represents Sr, Ce or Ca;

symbol C represents Cr, Mn, Fe, Co, Ti, or Zr, symbol D represents Cr, Ni, Zr, Ce, Fe, Al, or Co being different from symbol C, and symbol P represents La, Pr, Nd, Sm, Eu, Gd, Tb, Dy, Tm, Yb, Ca, Y, Sr, Ba, Zr, Mn, Fe, or Cr, wherein X satisfies the condition of $0 \leq X \leq 0.5$ and Y satisfies the condition of $0 \leq Y \leq 0.5$.

18. A sensor as in claim 4, wherein the inactive electrode is inactive for promoting oxidation of hydrocarbon gas but has activity for promoting oxidation of hydrogen gas and carbon monoxide gas.

* * * * *